US011395805B2

(12) United States Patent
Mao et al.

(10) Patent No.: US 11,395,805 B2
(45) Date of Patent: *Jul. 26, 2022

(54) METHODS OF PREPARING POLYELECTROLYTE COMPLEX NANOPARTICLES

(71) Applicant: The Johns Hopkins University, Baltimore, MD (US)

(72) Inventors: Hai-Quan Mao, Baltimore, MD (US); Jose Luis Santos, Rockville, MD (US); Yong Ren, Baltimore, MD (US); John-Michael Williford, Chicago, IL (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/587,608

(22) Filed: Sep. 30, 2019

(65) Prior Publication Data

US 2020/0101023 A1     Apr. 2, 2020

Related U.S. Application Data

(63) Continuation of application No. 15/221,189, filed on Jul. 27, 2016, now Pat. No. 10,441,549.

(60) Provisional application No. 62/346,001, filed on Jun. 6, 2016, provisional application No. 62/301,149, filed on Feb. 29, 2016, provisional application No. 62/204,739, filed on Aug. 13, 2015.

(51) Int. Cl.
*A61K 47/61* (2017.01)
*A61K 9/51* (2006.01)
*A61K 47/64* (2017.01)

(52) U.S. Cl.
CPC .......... *A61K 9/5192* (2013.01); *A61K 9/5115* (2013.01); *A61K 9/5146* (2013.01); *A61K 9/5161* (2013.01); *A61K 9/5169* (2013.01); *A61K 47/61* (2017.08); *A61K 47/6455* (2017.08)

(58) Field of Classification Search
CPC .. A61K 47/61; A61K 47/6455; A61K 9/5115; A61K 9/5146; A61K 9/5161; A61K 9/5169; A61K 9/5192
See application file for complete search history.

(56) References Cited

U.S. PATENT DOCUMENTS

2013/0108774 A1   5/2013 Mueller

FOREIGN PATENT DOCUMENTS

| WO | WO 2008/033497 | 3/2008 | |
| WO | WO-2014197970 A1 * | 12/2014 | ......... A61K 48/0041 |
| WO | WO 2015/061768 | 4/2015 | |

OTHER PUBLICATIONS

Akbulut et al., Generic Method of Preparing Multifunctional Fluorescent Nanoparticles Using Flash NanoPrecipitation. Adv. Funct. Mater. 2009;19:718-25.
Baum, C. et al., Mutagenesis and Oncogenesis by Chromosomal Insertion of Gene Transfer Vectors, Human Gene Therapy, Mar. 2006, vol. 17, pp. 253-263.
Beh, C. W. et al., Direct interrogation of DNA content distribution in nanoparticles by a novel microfluidics-based single particle analysis, Nano Lett, 2014, 14, 4729-35.
Bertrand, N. et al., Cancer Nanotechnology: The Impact of Passive and Active Targeting in the Era of Modern Cancer Biology, Advanced Drug Delivery Reviews 2014, 66, 2; V. P. Chauhan, R. K. Jain, Nature Materials 2013, 12, 958.
Bessis, N. et al., Immune Responses to Gene Therapy Vectors: Influence on Vector Function and Effector Mechanisms, Gene Therapy, 2004, 11 Suppl 1, S10-17.
Bonnet et al., Systemic delivery of DNA or siRNA mediated by linear polyethylenimine (L-PEI) does not induce an inflammatory response. Pharm Res. Dec. 2008;25(12):2972-82.
Buchhammer et al., Preparation of monodisperse polyelectrolyte complex nanoparticles in dilute aqueous solution. Progr Colloid Polym Sci. 2004;124:98-102.
Buscail, L. et al., First-in-man Phase 1 Clinical Trial of Gene Therapy for Advanced Pancreatic Cancer: Safety, Biodistribution, and Preliminary Clinical Findings, Molecular Therapy, Apr. 2015, vol. 23, No. 4, pp. 779-789.
Chauhan, V. P. et al., Strategies for Advancing Cancer Nanomedicine, Nature Materials, Nov. 2013, vol. 12, pp. 958-962.
D'Addio et al., Controlling drug nanoparticle formation by rapid precipitation. Adv Drug Deliv Rev. May 30, 2011;63(6):417-26.
D'Addio, S. M. et al., Effects of Block Copolymer Properties on Nanocarrier Protection from in vivo Clearance, Journal of Controlled Release: Official Journal of the Controlled Release Society, Aug. 2012, vol. 162, pp. 208-217.
D'Addio, S.M. et al., Optimization of Cell Receptor Specific Targeting Through Multivalent Surface Decoration of Polymeric Nanocarriers, Journal of Controlled Release: Official Journal of the Controlled Release Society May 2013, vol. 168, pp. 41-49.
Gindy et al., Preparation of poly(ethylene glycol) protected nanoparticles with variable bioconjugate ligand density. Biomacromolecules. Oct. 2008;9(10):2705-11.
Ginn et al., Gene therapy clinical trials worldwide to 2012—an update. J Gene Med. Feb. 2013;15(2):65-77.

(Continued)

*Primary Examiner* — Irina S Zemel
(74) *Attorney, Agent, or Firm* — Casimir Jones, S.C.; Jeffrey W. Childers

(57) ABSTRACT

The presently disclosed subject matter provides methods for continuously generating uniform polyelectrolyte complex (PEC) nanoparticles comprising: flowing a first stream comprising one or more water-soluble polycationic polymers at a first variable flow rate into a confined chamber; flowing a second stream comprising one or more water-soluble polyanionic polymers at a second variable flow rate into the confined chamber; and impinging the first stream and the second stream in the confined chamber until the Reynolds number is from about 1,000 to about 20,000, thereby causing the one or more water-soluble polycationic polymers and the one or more water-soluble polyanionic polymers to undergo a polyelectrolyte complexation process that continuously generates PEC nanoparticles. Compositions produced from the presently disclosed methods and a device for producing the compositions are also disclosed.

18 Claims, 27 Drawing Sheets
(14 of 27 Drawing Sheet(s) Filed in Color)

(56) References Cited

OTHER PUBLICATIONS

Han et al., A Simple Confined Impingement Jets Mixer for Flash Nanoprecipitation. J Pharm Sci. 2012;101:4018-23.

Han, J. et al., A simple confined impingement jets mixer for flash nanoprecipitation, J Pharm Sci-US, Oct. 2012, vol. 101, No. 10, pp. 4018-4023.

Ho et al., Tuning physical properties of nanocomplexes through microfluidics-assisted confinement. Nano Lett. May 11, 2011;11(5):2178-82.

Jere et al., Degradable polyethylenimines as DNA and small interfering RNA carriers. Expert Opin Drug Deliv. Aug. 2009;6(8):827-34.

Johnson et al., Mechanism for rapid self-assembly of block copolymer nanoparticles. Phys Rev Lett. Sep. 12, 2003;91(11):118302.

Johnson et al., Chemical processing and micromixing in confined impinging jets. AIChE Journal Apr. 2004;49(9):2264-82.

Johnson et al., Flash NanoPrecipitation of Organic Actives and Block Copolymers using a Confined Impinging Jets Mixer. Aust. J. Chem. 2003;56:1021-4.

Kamaly, N. et al., Targeted polymeric therapeutic nanoparticles: design, development and clinical translation, Chemical Society Reviews, Apr. 2012, vol. 41, pp. 2971-3010.

Kolishetti, N., Engineering of self-assembled nanoparticle platform for precisely controlled combination drug therapy, Proceedings of the National Academy of Sciences of the United States of America, Oct. 2010, vol. 107, No. 42, pp. 17939-44.

Lewis, D. R., Sugar-Based Amphiphilic Nanoparticles Arrest Atherosclerosis in Vivo, P Natl Acad Sci USA, Mar. 2015, vol. 112, No. 9, pp. 2693-2698.

Lim et al., Ultra-high throughput synthesis of nanoparticles with homogeneous size distribution using a coaxial turbulent jet mixer. ACS Nano. Jun. 24, 2014;8(6):6056-65.

Luo et al., Toroidal structures from brush amphiphiles. Chem Commun (Camb). Jan. 18, 2014;50(5):536-8.

Mangraviti, A. et al., Polymeric Nanoparticles for Nonviral Gene Therapy Extend Brain Tumor Survival in Vivo, ACS Nano, 2015, vol. 9, No. 2, pp. 1236-1249.

Mastorakos, P. et al., Highly Compacted Biodegradable DNA Nanoparticles Capable of Overcoming the Mucus Barrier for Inhaled Lung Gene Therapy, Proceedings of the National Academy of Sciences of the United States of America, Jul. 2015, vol. 112, No. 28, pp. 8720-8725.

Muller et al., Polyelectrolyte Complex Nanoparticles of Poly(ethyleneimine) and Poly(acrylic acid): Preparation and Applications. Polymers 2011;3:762-778.

Mura et al., Stimuli-responsive nanocarriers for drug delivery. Nat Mater. Nov. 2013;12(11):991-1003.

Murday et al., Translational nanomedicine: status assessment and opportunities. Nanomedicine. Sep. 2009;5(3):251-73.

Pack et al., Design and development of polymers for gene delivery. Nat Rev Drug Discov. Jul. 2005;4(7):581-93.

Patnaik et al., Novel polyethylenimine-derived nanoparticles for in vivo gene delivery. Expert Opin Drug Deliv. Feb. 2013;10(2):215-28.

Peer et al., Nanocarriers as an emerging platform for cancer therapy. Nat Nanotechnol. Dec. 2007;2(12):751-60.

Romanowsky et al., High throughput production of single core double emulsions in a parallelized microfluidic device. Lab Chip. Feb. 21, 2012;12(4):802-7.

Santos et al., Kinetically Arrested Assemblies of Architecturally Distinct Block Copolymers. Macromolecules 2014;47:137-45.

Shen et al., Self-assembling process of flash nanoprecipitation in a multi-inlet vortex mixer to produce drug-loaded polymeric nanoparticles. J Nanopart Res. 2011;13:4109-20.

Valencia, P. et al., Microfluidic Technologies for Accelerating the Clinical Translation of Nanoparticles, Nat Nanotechnol, Oct. 2012, vol. 7, pp. 623-629.

Wrightman et al., Different behavior of branched and linear polyethylenimine for gene delivery in vitro and in vivo. J Gen Med. 2001;3:362-72.

Yang, J. et al., A Nanoparticle Formulation that Selectively Transfects Metastatic Tumors in Mice, P Natl Acad Sci USA, Sep. 2013, vol. 110, No. 36, pp. 14717-14722.

Yin et al., Non-viral vectors for gene-based therapy. Aug. 2014;15:541-55.

Zhu et al., Polyelectrolyte Stabilized Drug Nanoparticles via Flash Nanoprecipitation: A Model Study With beta-Carotene. J Pharm Sci. Oct. 2010;99(10):4295-4306.

Zhu, Z., Flash Nanoprecipitation: Prediction and Enhancement of Particle Stability via Drug Structure, Molecular Pharmaceutics, 2014, vol. 11, pp. 776-786.

European Extended Search Report for EP16835614.5, dated Feb. 25, 2019, 8 pages.

International Search Report and Written Opinion for PCT/US2016/044185, dated Dec. 8, 2016, 14 pages.

* cited by examiner

METHODS OF PREPARING POLYELECTROLYTE COMPLEX NANOPARTICLES

CROSS-REFERENCE TO RELATED APPLICATIONS

This application is a continuation of U.S. patent application Ser. No. 15/221,189, filed Jul. 27, 2019, now U.S. Pat. No. 10,441,549, which claims the benefit of U.S. Provisional Application Nos. 62/346,001 filed Jun. 6, 2016, 62/301,149 filed Feb. 29, 2016, and 62/204,739 filed Aug. 13, 2015, the contents of each are incorporated herein by reference in their entirety.

FEDERALLY SPONSORED RESEARCH OR DEVELOPMENT

This invention was made with government support under R21EB013274 and R02E018358 awarded by the National Institutes of Health (NIH). The government has certain rights in the invention.

BACKGROUND

The prospect of developing a gene therapy for the detection and treatment of disease remains high for a number of clinical applications, including cancer, immunodeficiency, and metabolic disorders (Ginn et al., 2013; Peer et al., 2007). Viral-based delivery systems comprise the majority of gene carriers used in gene therapy clinical trials to date; safety concerns, however, motivate the need to engineer alternate delivery systems (Ginn et al., 2013; Yin et al., 2014). Non-viral gene delivery methods have been developed to overcome the main limitations associated with viruses, such as the potential for fatal systemic immune responses, insertional mutagenesis, limited DNA vector size, and issues with large-scale production of viruses (Yin et al., 2014; Baum et al., 2004).

Polymeric nanoparticles are the most widely used non-viral carriers, owing to their protecting the DNA from degradation, and improving intracellular delivery and transfection efficiency of the gene of interest (Bertrand et al., 2005; Mura et al., 2005; Bonnet et al., 2008). Polyelectrolyte complexes (PECs) have been used for drug delivery due to their ability to entrap therapeutic agents.

Of all polymers developed for gene therapy applications, linear polyethylenimine (/PEI) is often utilized because it exhibits high gene delivery efficiency both in vitro and in vivo. Furthermore, compared to its branched PEI counterpart, /PEI has a better safety profile (Bonnet et al., 2008; Jere et al., 2001; Patnaik et al., 2001). It has also been tested in several clinical trials (e.g., NCT01274455 and NCT00595088), primarily through tissue-specific administration routes (Buscail et al., 2015). While there has been increasing efforts to improve the physico-chemical properties and biological performance of /PEI as DNA delivery carrier though molecular engineering and nanoparticle optimization, the progress to clinical application has been hindered by the lack of reproducible and scalable methods for assembly of these complex nanomaterials.

Bulk mixing in the form of vortexing or pipetting are widely used in laboratory environments; but due to their poor micromixing environment, they often lead to high degrees of variability within a preparation batch or between batches as a result of uncontrollable aggregates (Mangraviti et al., 2013; Mangraviti et al., 2015; Mastorakos et al., 2009; Mastorakos et al., 2015; Valencia et al., 2012; Yang et al., 2013; Murday et al., 2009). For example, a recent study reported that batch volume of the nanoparticle preparation by conventional bulk methods significantly affected PEI/siRNA nanoparticle size, with larger preparation solution volumes leading to larger and wider range of particle sizes (Lim et al., 2014). Therefore, developing production methods by which DNA nanoparticles properties can be reproducibly tuned without compromising the biological performance is paramount.

Microfluidic devices with different designs have been reported aiming at delivering better control over particle size and its distribution. For instance, /PEI/siRNA nanoparticles prepared by a microfluidic device displayed significantly higher gene knockdown efficiency in vitro compared to those prepared by bulk mixing (Lim et al., 2014). Furthermore, nanoparticle properties did not change when the batch size of microfluidic mixing was varied. Another study used microfluidics-assisted confinement to prepare polycation/DNA nanocomplexes (Ho et al., 2011). Compared to bulk preparation, microfluidic preparation led to decrease in nanoparticle size distribution, yielding highly condensed, compact and stable nanostructures, reduction in cytotoxicity, and an enhancement of in vitro transfection efficiency. Microfluidic systems, however, can have some limitations, such as the need to formulate complex materials for nanoparticle formulation as well as a limited production capacity (<7.2 g per day) due to the small size of the microfluidic channels (Kolishetti et al., 2010; Romanowsky et al., 2012).

Flash nanoprecipitation (FNP) offers a continuous and scalable process that has been used for the production of block copolymer nanoparticles. This process uses rapid micromixing conditions (on the order of 1 msec) to establish homogeneous supersaturation conditions and controlled precipitation of hydrophobic solutes (organic or inorganic) using block copolymer self-assembly (Johnson et al., Aust. J. Chem., 2003; Johnson et al., Phys. Rev. Lett., 2003; Johnson et al., Aiche J., 2003; Shen et al., 2011). Compared to bulk preparation methods, this process allows for the formation of uniform aggregates with tunable size in a continuous flow operation process, which is amenable for scale-up production. This process also offers a higher degree of versatility and control over particle size and distribution, higher drug encapsulation efficiency, and improved colloidal stability (Shen et al., 2011; D'Addio et al., 2013; D'Addio et al., 2011; D'Addio et al., 2012; Gindy et al., 2008; Lewis et al., 2015; Luo et al., 2014; Santos et al., 2014).

However, in contrast to block copolymer nanoparticles, the assembly of polyelectrolyte complexes is driven by a "complexation reaction", which is far different from the assembly of amphiphilic copolymers in aqueous media by the FNP method. It appears unlikely that such PEC nanoparticles can be predictably assembled with the FNP method. Hence, there remains a desire in the art to find methods for preparing PEC nanoparticles, which result in properties comparable to those for block copolymer nanoparticles using FNP.

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact-.shtml.

In some aspects, the presently disclosed subject matter provides a flash nanocomplexation (FNC) method of continuously generating uniform polyelectrolyte complex (PEC) nanoparticles, the method comprising: (a) flowing a first stream comprising one or more water-soluble polycationic polymers at a first variable flow rate into a confined chamber; (b) flowing a second stream comprising one or more water-soluble polyanionic polymers at a second variable flow rate into the confined chamber; and (c) impinging the first stream and the second stream in the confined chamber until the Reynolds number is from about 1,000 to about 20,000, thereby causing the one or more water-soluble polycationic polymers and the one or more water-soluble polyanionic polymers to undergo a polyelectrolyte complexation process that continuously generates PEC nanoparticles.

In some aspects, the presently disclosed subject matter provides a uniform polyelectrolyte complex (PEC) nanoparticle preparation generated from a flash nanocomplexation (FNC) method, the method comprising: flowing a first stream comprising one or more water-soluble polycationic polymers at a first variable flow rate into a confined chamber; flowing a second stream comprising one or more water-soluble polyanionic polymers at a second variable flow rate into the confined chamber; and impinging the first stream and the second stream in the confined chamber until the Reynolds number is from about 1,000 to about 20,000, thereby causing the one or more water-soluble polycationic polymers and the one or more water-soluble polyanionic polymers to undergo a polyelectrolyte complexation process that continuously generates PEC nanoparticles.

In some embodiments, the first stream and the second stream are on opposing sides when entering the confined chamber, and wherein the ratio of the flow rate of the second stream to the flow rate of the first stream is from about 1 to about 10. In some embodiments, the first stream and/or the second stream further comprise one or more water-soluble therapeutic agents.

In some embodiments, the methods further comprise flowing a third stream into the confined chamber, wherein each stream is equidistant from the other two streams when entering the confined chamber. In some embodiments, the third stream comprises one or more water-soluble therapeutic agents, one or more miscible organic solvents, and/or one or more cryoprotectants.

In some embodiments, the generated PEC nanoparticles encapsulate at least one or more water-soluble therapeutic agents. In some embodiments, one or more water-soluble therapeutic agents are selected from the group consisting of a small molecule, carbohydrate, sugar, protein, peptide, nucleic acid, antibody or antibody fragment thereof, hormone, hormone receptor, receptor ligand, cytokine, and growth factor.

In some embodiments, one or more water-soluble polycationic polymers are selected from the group consisting of chitosan, PAMAM dendrimers, polyethylenimine (PEI), protamine, poly(arginine), poly(lysine), poly(beta-aminoesters), cationic peptides and derivatives thereof.

In some embodiments, one or more water-soluble polyanionic polymers are selected from the group consisting of poly(aspartic acid), poly(glutamic acid), negatively charged block copolymers, heparin sulfate, dextran sulfate, hyaluronic acid, alginate, tripolyphosphate (TPP), oligo (glutamic acid), a cytokine, a protein, a peptide, a growth factor, and a nucleic acid.

In some embodiments, the nucleic acid is selected from the group consisting of an antisense oligonucleotide, cDNA, genomic DNA, guide RNA, plasmid DNA, vector DNA, mRNA, miRNA, piRNA, shRNA, and siRNA.

In some embodiments, the first variable flow rate, the second variable flow rate, and the third variable flow rate if present are greater than about 5 milliliters/minute. In some embodiments, the Reynolds number ranges from about 2,000 to about 8,000. In some embodiments, the Reynolds number ranges from about 3,000 to about 5,000. In some embodiments, the pH value of the first stream and the pH value of the second stream range from about 2.5 to about 8.4. In some embodiments, the pH value of the first stream and the pH value of the second stream range from about 3.5 to about 7.4.

In some embodiments, the generated polyelectrolyte complex (PEC) nanoparticles range in size from about 20 nm to about 500 nm in diameter. In some embodiments, the generated polyelectrolyte complex (PEC) nanoparticles range in size from about 25 nm to about 100 nm in diameter. In some embodiments, the generated polyelectrolyte complex (PEC) nanoparticles range in size from about 25 nm to about 60 nm in diameter. In some embodiments, the generated polyelectrolyte complex (PEC) nanoparticles are about 30 nm to about 45 nm in diameter. In some embodiments, the generated polyelectrolyte complex (PEC) nanoparticles are about 30 nm in diameter. In some embodiments, the polydispersity index of the generated polyelectrolyte complex (PEC) nanoparticles ranges from about 0.05 to about 0.1.

In some embodiments, the one or more water-soluble polyanionic polymers is plasmid DNA and the one or more water-soluble polycationic polymers is selected from the group consisting of linear polyethylenimine (PEI) and its derivatives.

In some embodiments, the second stream comprises one or more water-soluble therapeutic agents and the polyelectrolyte complexation process encapsulates one or more water-soluble therapeutic agents in the generated polyelectrolyte complex (PEC) nanoparticles.

In some embodiments, the first stream comprises chitosan and the second stream comprises tripolyphosphate (TPP) and a protein, wherein the protein is co-encapsulated by the TPP and chitosan in the generated polyelectrolyte complex (PEC) nanoparticles.

In some aspects, the presently disclosed subject matter provides a device for continuously generating uniform polyelectrolyte complex (PEC) nanoparticles, the device comprising: (a) a housing comprising: (i) a confined chamber; (ii) a first inlet configured to permit a first stream comprising one or more water-soluble polycationic polymers to flow into the confined chamber; (iii) a second inlet configured to permit a second stream comprising one or more water-soluble polyanionic polymers to flow into the confined chamber; and (iv) optionally a third inlet configured to permit a third stream to flow into the confined chamber; (b) a first conduit providing a first stream path configured to permit the first stream to flow into the confined chamber at a first variable flow rate through the first inlet, wherein the first conduit has a first variable diameter; (c) a second conduit providing a second stream path configured to permit the second stream to flow into the confined chamber at a second variable flow rate through the second inlet, wherein the second conduit has a second variable diameter; and (d) optionally a third conduit providing a third stream path configured to permit the third stream to flow into the confined chamber at a third variable flow rate through the third inlet, wherein the third conduit has a third variable diameter; wherein the first conduit, the second conduit, and the third conduit if present, are situated equidistantly relative to each other on an exterior surface of the housing in a manner that permits impinging of the streams in the confined chamber until the Reynolds number is from about 1,000 to about 20,000, thereby causing the one or more water-soluble polycationic polymers and the one or more water-soluble polyanionic polymers to undergo a polyelectrolyte complexation process that continuously generates PEC nanoparticles.

In some embodiments, the confined chamber is a circular cylinder ranging in diameter from about 1.25 mm to about 7.5 mm and ranging in height from about 2.5 mm to about 15 mm. In some embodiments, the first conduit, the second conduit, and the third conduit if present extend from the exterior of the housing, into the inlet, and to the confined chamber.

In some embodiments, the first conduit, the second conduit, and the third conduit if present each have a first section with a diameter d2 in fluid communication with a second section with a diameter d1 in fluid communication with the confined chamber, wherein the diameter d1 ranges from about 0.25 mm to about 1.5 mm and the ratio of the diameter d2 to the diameter d1 ranges from about 1.5 to about 3.0. In some embodiments, the first conduit, the second conduit, and the third conduit if present each have a first section with a diameter d2 in fluid communication with a second section with a diameter d1 in fluid communication with the confined chamber, wherein the diameter d1 ranges from about 0.25 mm to about 1.5 mm and the ratio of the diameter d2 to the diameter d1 ranges from about 1.8 to about 2.5. In some embodiments, the first conduit, the second conduit, and the third conduit if present each have a first section with a diameter d2 in fluid communication with a second section with a diameter d1 in fluid communication with the confined chamber, wherein the diameter d1 ranges from about 0.25 mm to about 1.5 mm and the ratio of the diameter d2 to the diameter d1 is about 2.0.

In some embodiments, the first conduit, the second conduit, and the third conduit if present each have a first section with a diameter d2 in fluid communication with a second section with a diameter d1 in fluid communication with the confined chamber, wherein the first section and the second section are inside the housing and external to the confined chamber.

In some embodiments, the third conduit is present. In some embodiments, the impinged streams comprise a mixed solution containing the generated PEC nanoparticles, and the housing further comprises at least one outlet configured to remove the mixed solution containing the generated PEC nanoparticles from the device after impinging of the streams occurs in the confined chamber.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below

BRIEF DESCRIPTION OF THE DRAWINGS

The patent or application file contains at least one drawing executed in color. Copies of this patent or patent application publication with color drawings will be provided by the Office upon request and payment of the necessary fee.

Figure 1A:
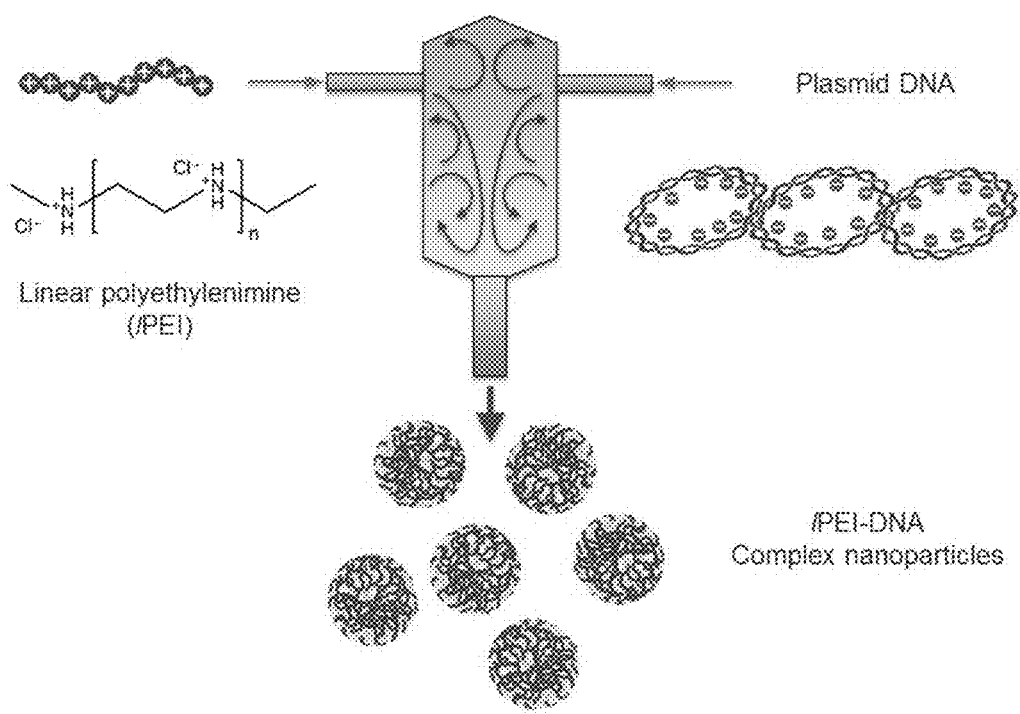
Figure 1B:
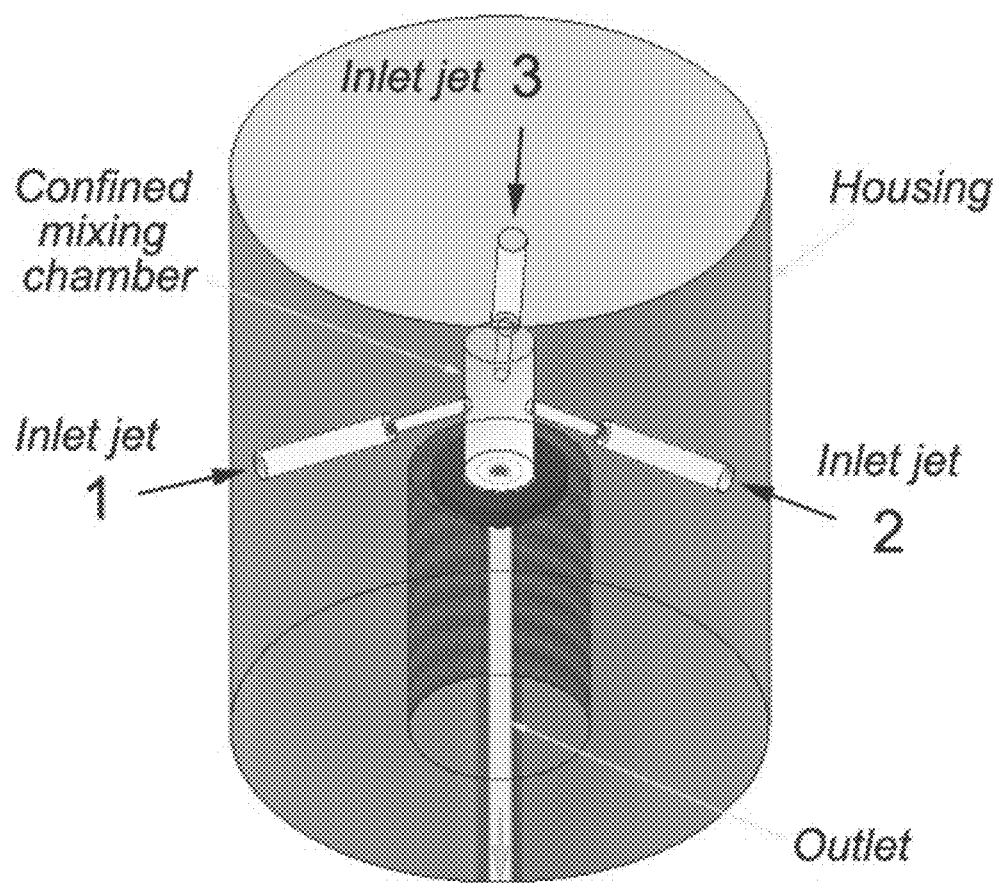
Figure 1C:
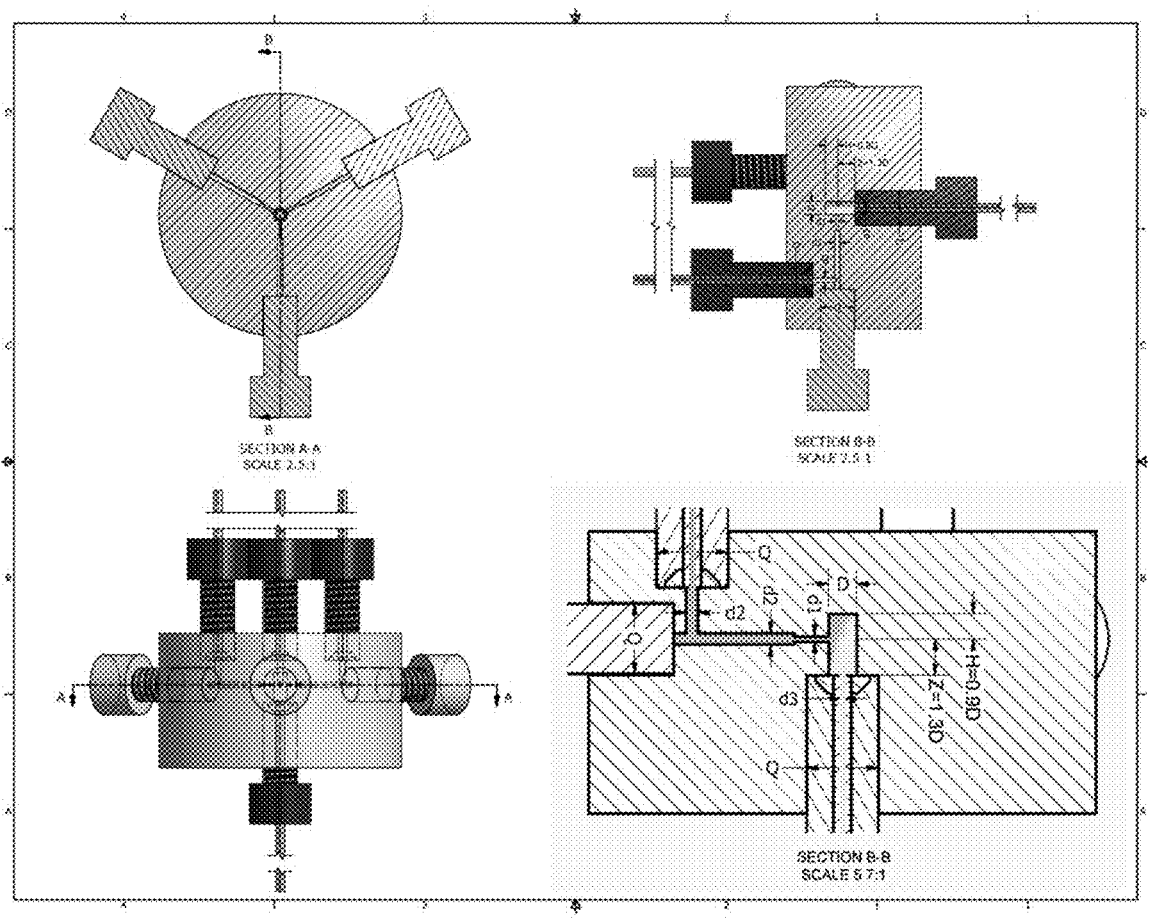
Figure 1D:
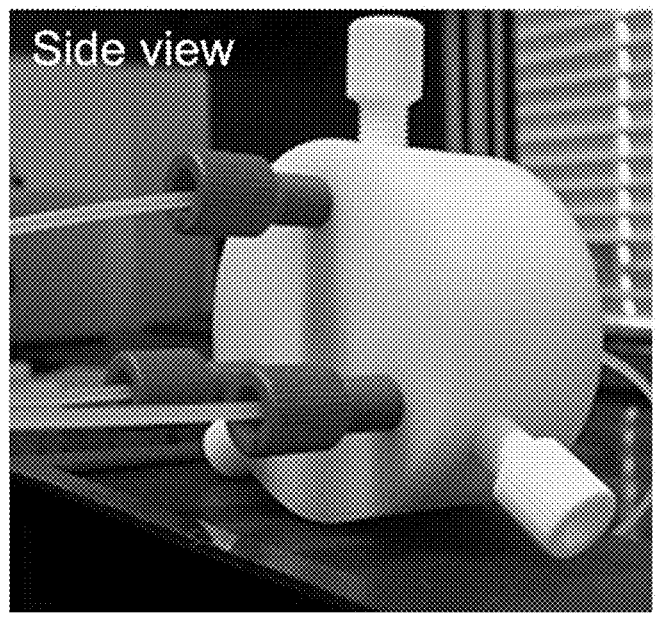
Figure 1E:
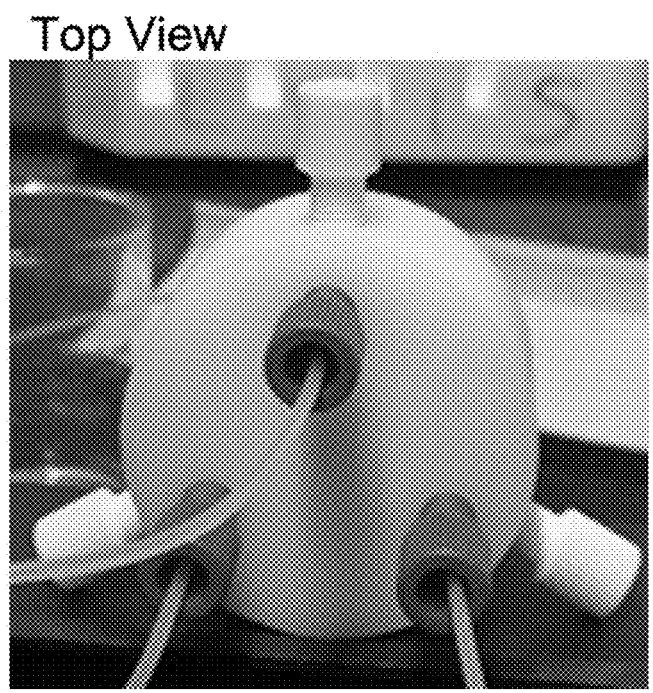
Figure 2A:
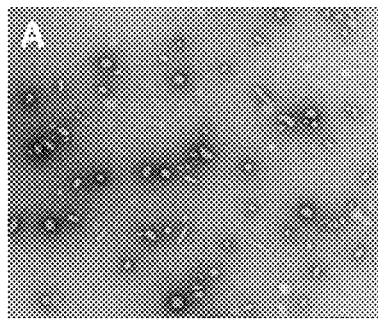
Figure 2B:
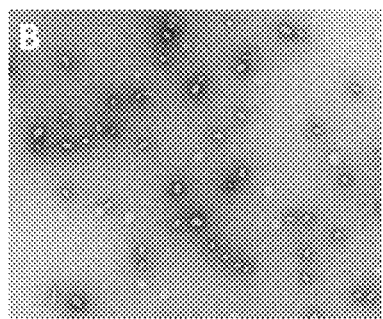
Figure 2C:
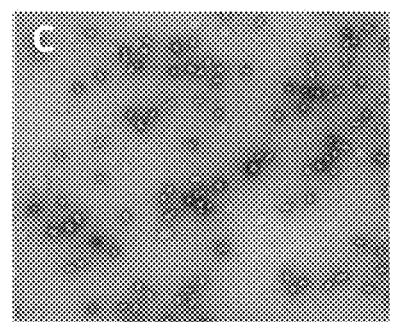
Figure 2D:
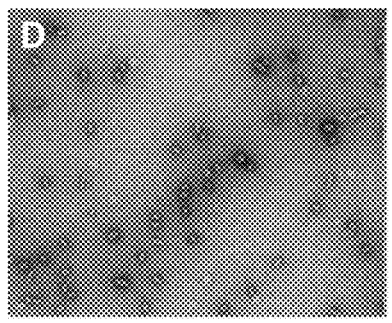
Figure 2E:
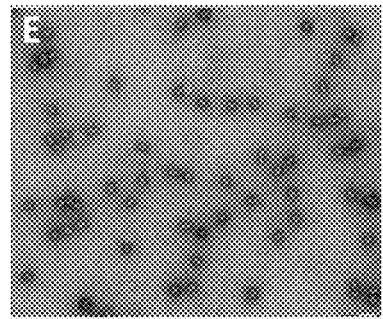
Figure 2F:
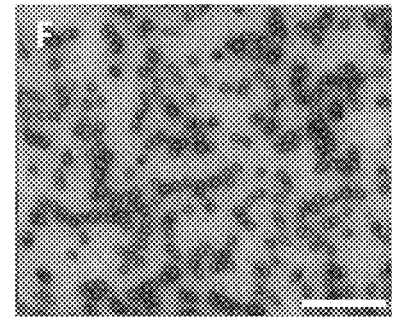
Figure 3A:
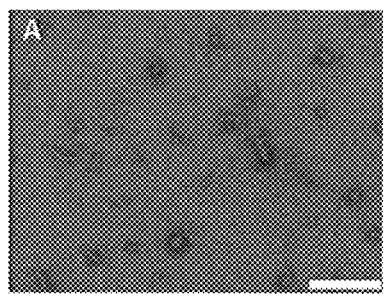
Figure 3B:
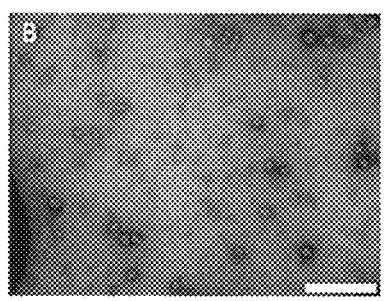
Figure 3C:
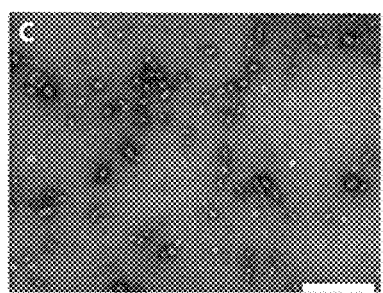
Figure 3D:
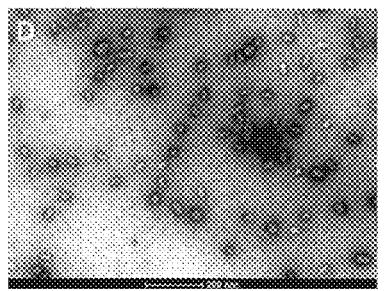
Figure 3E:
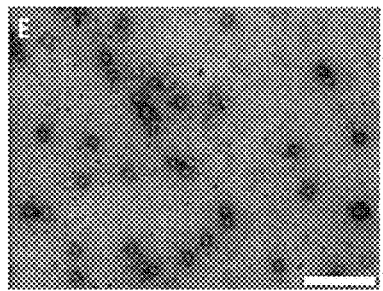
Figure 3F:
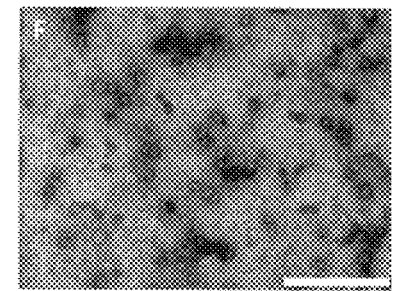
Figure 4A:
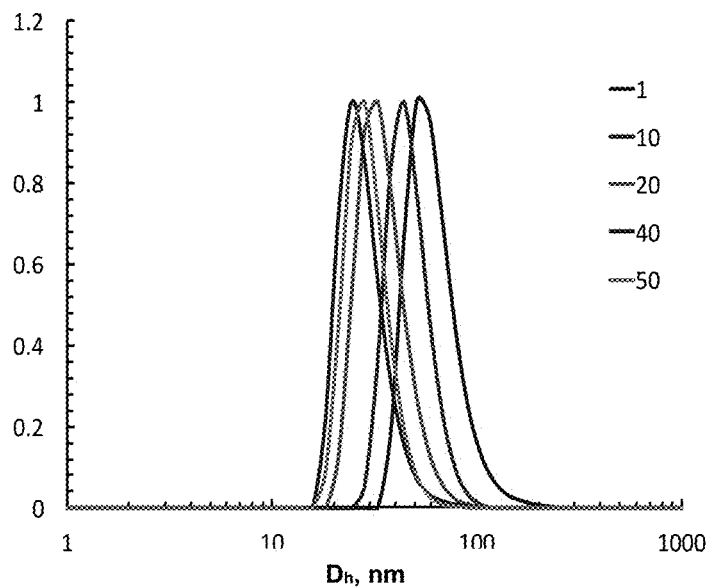
Figure 4B:
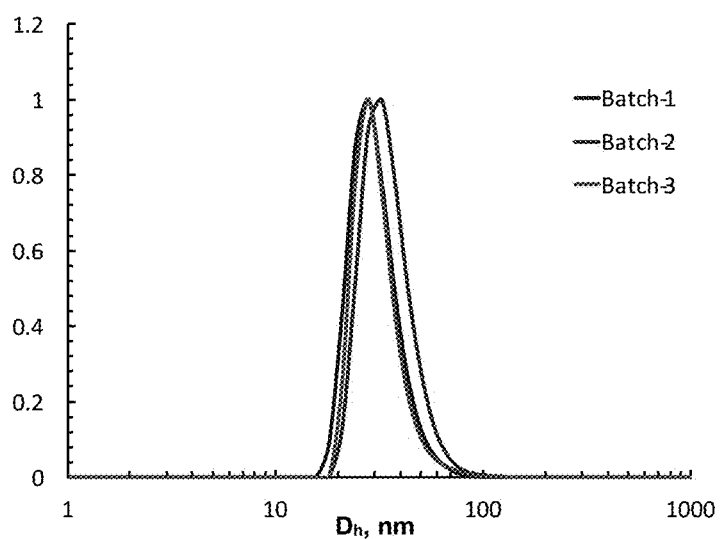
Figure 5A:
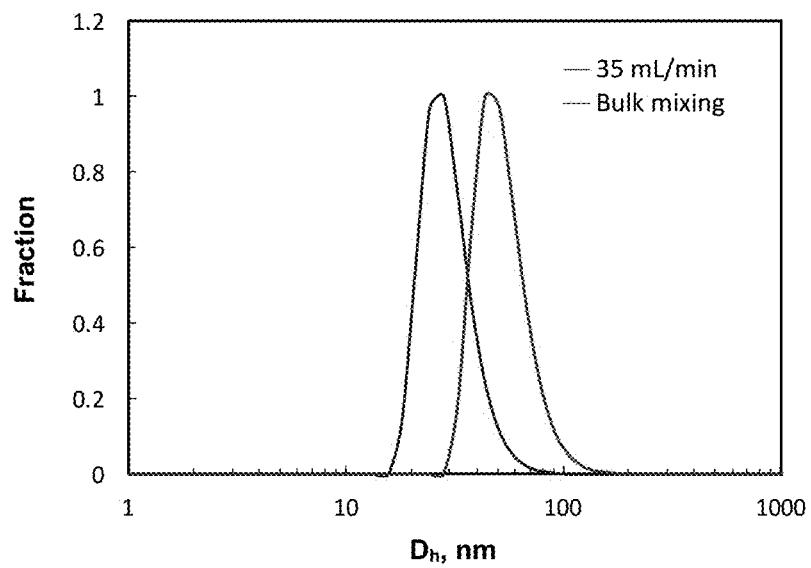
Figure 5B:
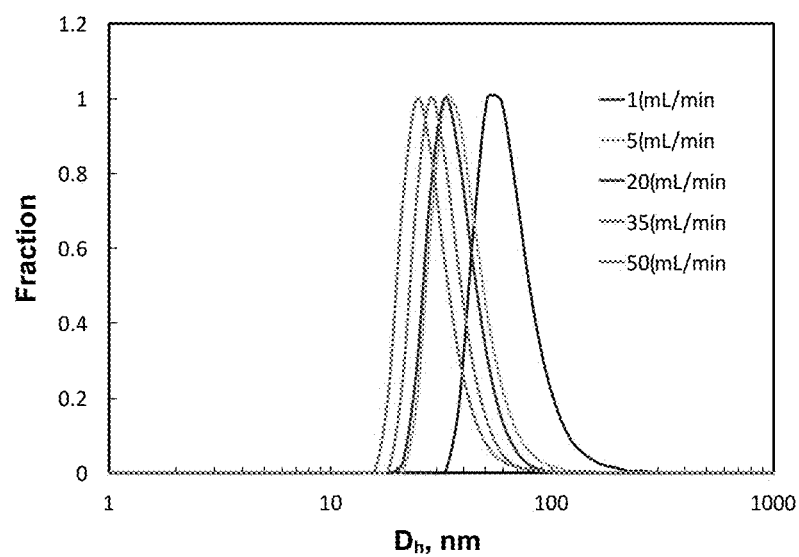
Figure 6A:
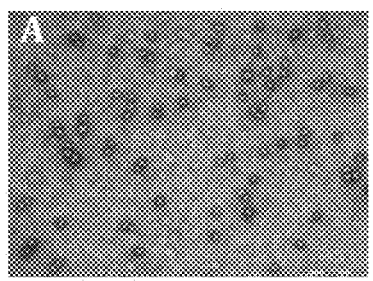
Figure 6B:
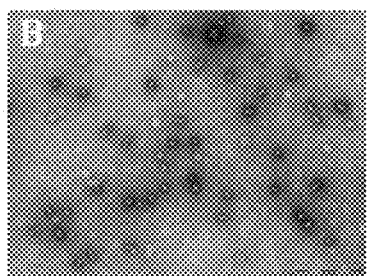
Figure 6C:
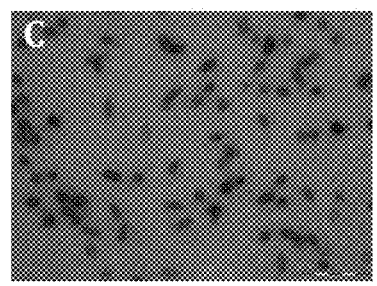
Figure 6D:
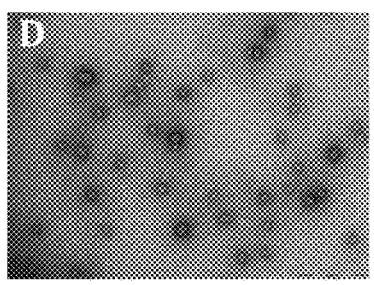
Figure 6E:
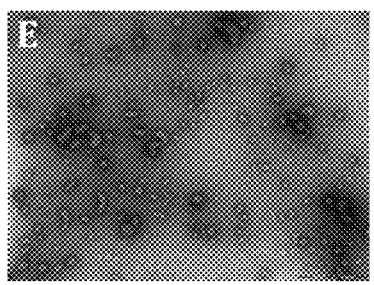
Figure 6F:
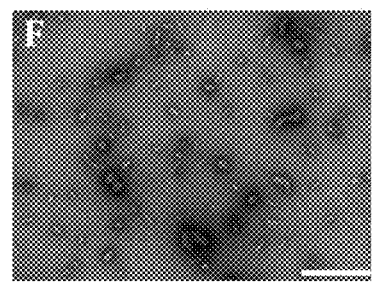
Figure 7A:
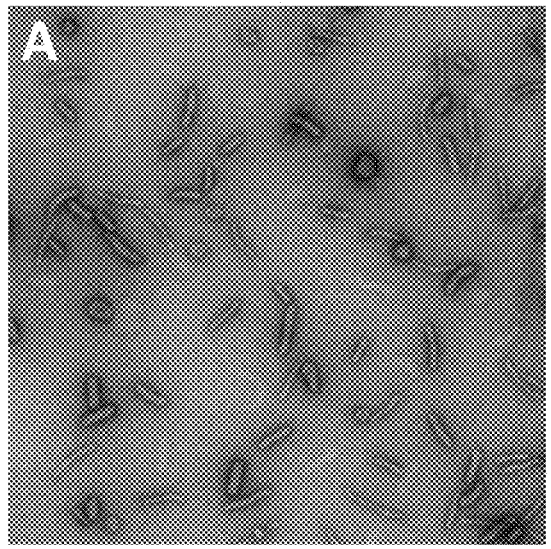
Figure 7B:
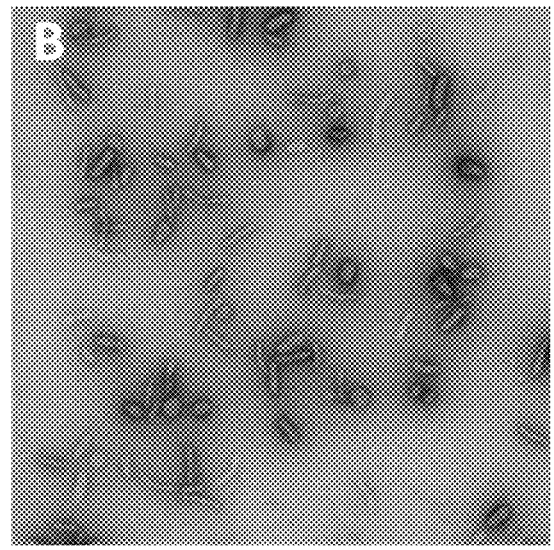
Figure 7C:
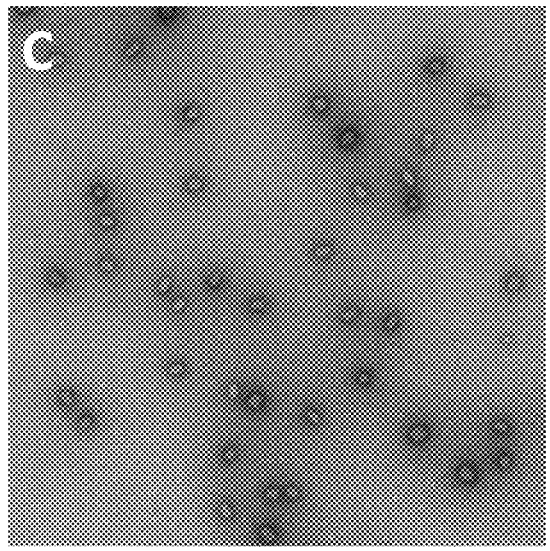
Figures 8A, 8B, 8C:
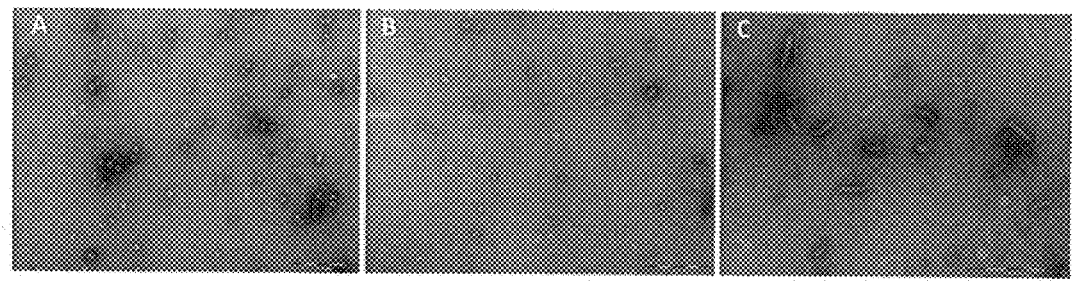
Figure 9A:
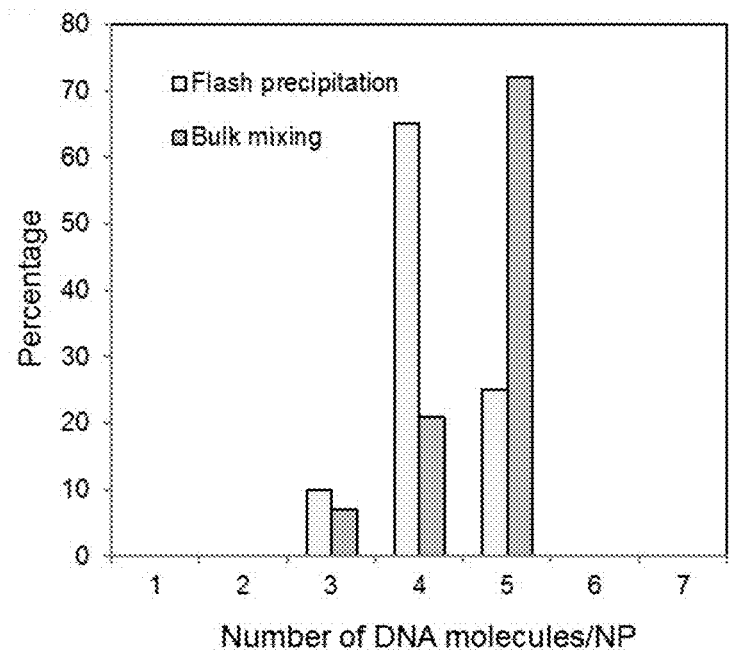
Figure 9B:
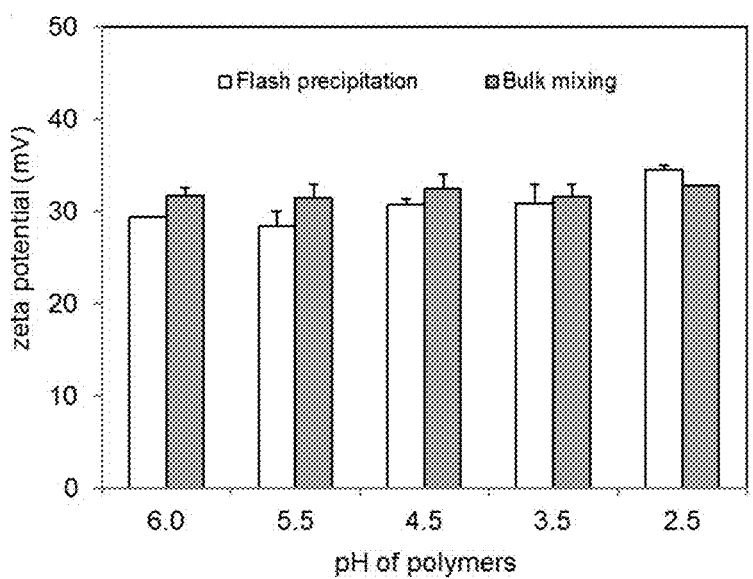
Figure 10:
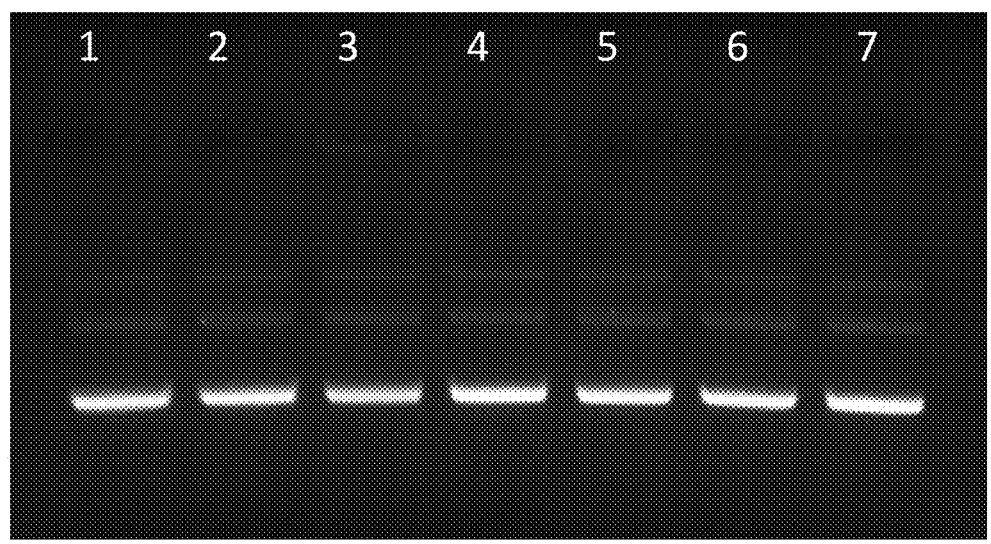

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, and FIG. 1E depict diagrams (FIG. 1A, FIG. 1B, and FIG. 1C) and photographs (FIG. 1D and FIG. 1E) of representative embodiments of the presently disclosed confined impinging jet (CIJ) device. FIG. 1A depicts an embodiment of the CIJ device used to fabricate polyelectrolyte complex (PEC) nanoparticles under rapid mixing conditions. Streams are independently loaded with linear polyethylenimine (/PEI) and plasmid DNA, and/PEI-DNA complex nanoparticles are formed in a small confined chamber before being collected; FIG. 1B depicts a schematic diagram showing a CIJ device with 3-jets separated by a 120° angle. Jet 1 can be loaded with positively charged polymers including chitosan, PAMAM dendrimers, PEI, protamine sulfate, poly(arginine, poly(lysine) and positively charged block copolymers. Jet 2 is charged with negatively charged macromolecules including poly(aspartic acid), heparin sulfate, dextran sulfate, hyaluronic acid, tripolyphosphate, oligo(glutamic acids), cytokines, proteins, peptides, growth factors, DNA, siRNA, mRNA. Jet 3 can be either capped or loaded with water miscible organic solvents to control the polarity of the final formulation in situ; FIG. 1C depicts an engineering drawing of the CIJ device used in the Examples; and FIG. 1D (side view) and FIG. 1E (top view) are photographs of an actual CIJ device (red inlets allow each stream to flow into the device, white ports are for drilling each stream path to the confined chamber and are typically blocked when the device is in use);

FIG. 2A, FIG. 2B, FIG. 2C, FIG. 2D, FIG. 2E, and FIG. 2F depict effects of the flow rate on particle size and distribution. /PEI-DNA complex nanoparticles were prepared at varying flow rates and analyzed by TEM. DNA concentration was 25 µg/mL, N/P=8 (N/P is amine:phosphate), and pH of /PEI solution was 3.5. TEM images of /PEI-DNA complex nanoparticles prepared at 5 mL/min (FIG. 2A), 10 mL/min (FIG. 2B), 20 mL/min (FIG. 2C), 30 mL/min (FIG. 2D), 40 mL/min (FIG. 2E), and 50 mL/min (FIG. 2F). Scale bar is 500 nm;

FIG. 3A, FIG. 3B, FIG. 3C, FIG. 3D, FIG. 3E, and FIG. 3F depict TEM images of /PEI 22 kDa:DNA nanoparticles prepared by bulk mixing in FIG. 3A, and under dynamic and controlled mixing in FIG. 3B, FIG. 3C, FIG. 3D, FIG. 3E, and FIG. 3F. Effect of the flow rate on IPEI:DNA nanoparticles: FIG. 3B, 1 mL/min, scale bar (sb) 200 nm; FIG. 3C, 10 mL/min, sb 200 nm; FIG. 3D, 20 mL/min; FIG. 3E, 35 mL/min, sb 200 nm; and FIG. 3F, 50 mL/min, sb 500 nm;

FIG. 4A and FIG. 4B depict an effect of the flow rate on number average size distribution of /PEI-DNA nanoparticles (FIG. 4A), and inter-batch variability for /PEI-DNA nanoparticles prepared at a flow rate of 40 mL/min (FIG. 4B). /PEI-DNA nanoparticles were prepared at an initial DNA concentration of 100 µg/mL, N/P=8, and pH of /PEI solution is 3.5;

FIG. 5A and FIG. 5B depict number average size distribution and the effect of flow rate on the size distribution. FIG. 5A depicts number average size distribution of /PEI 22 kDa:DNA nanoparticles prepared under bulk and dynamic mixing conditions; and FIG. 5B depicts the effect of flow rate on the size distribution of /PEI 22 kDa:DNA nanoparticles;

FIG. 6A, FIG. 6B, FIG. 6C, FIG. 6D, FIG. 6E, and FIG. 6F depict TEM images of /PEI-DNA complex nanoparticles prepared under fast mixing conditions (FIG. 6A, FIG. 6B, and FIG. 6C) in a CIJ and bulk mixing (FIG. 6D, FIG. 6E, and FIG. 6F) using different DNA concentrations. For fast mixing conditions, a flow rate of 20 mL/min was used. The pH of /PEI solutions was adjusted to 3.5 and an N/P ratio of 8 was used. Concentration of DNA used for complexation is 25 µg/mL (FIG. 6A, FIG. 6D), 50 µg/mL (FIG. 6B, FIG. 6E), and 100 µg/mL. Scale bar is 500 nm;

FIG. 7A, FIG. 7B, FIG. 7C, and FIG. 7D depict TEM images of /PEI-DNA complex nanoparticles of various shapes prepared under fast mixing conditions in a CIJ using PEI solutions of different pH. A flow rate of 20 mL/min, DNA concentration of 25 µg/mL and N/P=8 were used. FIG. 7A, pH of /PEI solution is 5.5; FIG. 7B, pH of /PEI solution is 4.5; FIG. 7C, the pH of /PEI solution is 3.5; and FIG. 7D, pH of /PEI solution is 2.5. Scale bar is 500 nm;

FIG. 8A, FIG. 8B, and FIG. 8C depict TEM images of IPEI 22 kDa:DNA nanoparticles of various shapes prepared under fast mixing conditions in a CIJ-3i and using PEI solutions of different pH. A flow rate of 37 mL/min was used. FIG. 8A, pH of PEI solution is 2.5; FIG. 8B, pH of PEI solution is 3.2; FIG. 8C, pH of PEI solution is 5.2;

FIG. 9A and FIG. 9B depict a physico-chemical characterization of /PEI-DNA complex nanoparticles generated under fast and bulk mixing conditions. FIG. 9A shows the distribution of DNA content for particles prepared under fast and bulk mixing conditions using Cylindrical Illumination Correlation Spectroscopy. The average number of DNA per particle was found to be 4.2 and 4.7 for fast and bulk mixing, respectively.

Figure 11:
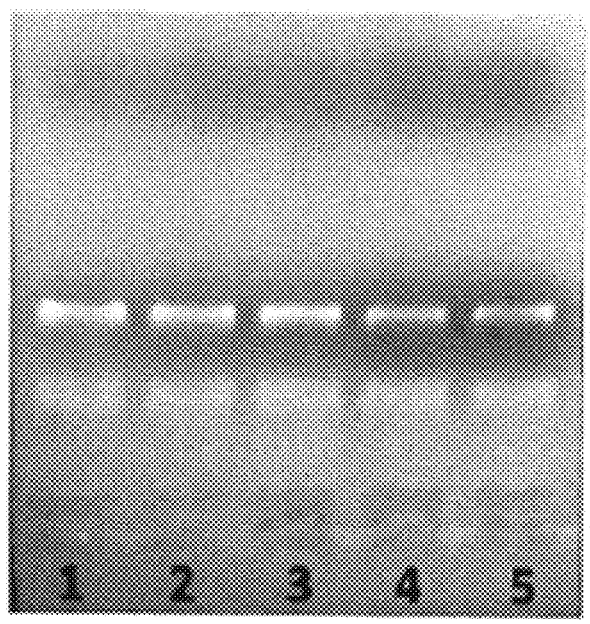
Figure 12A:
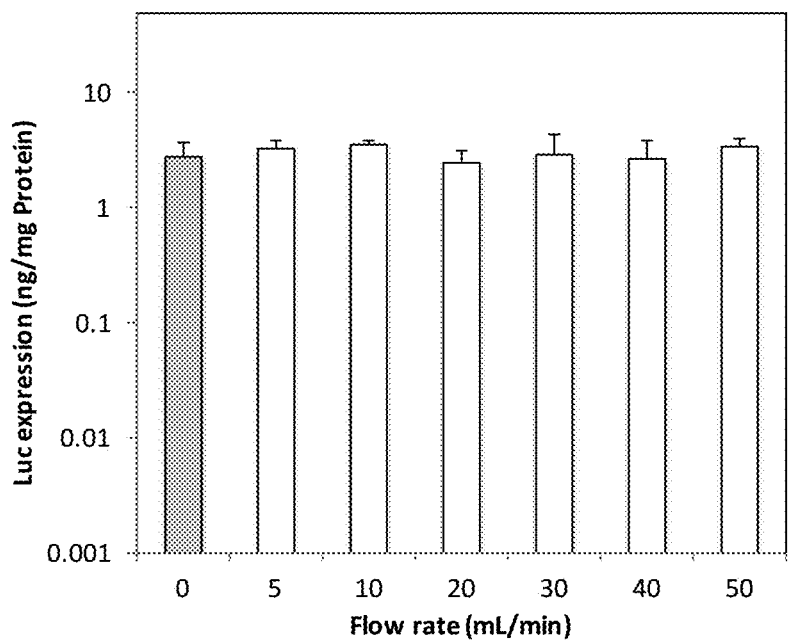
Figure 12B:
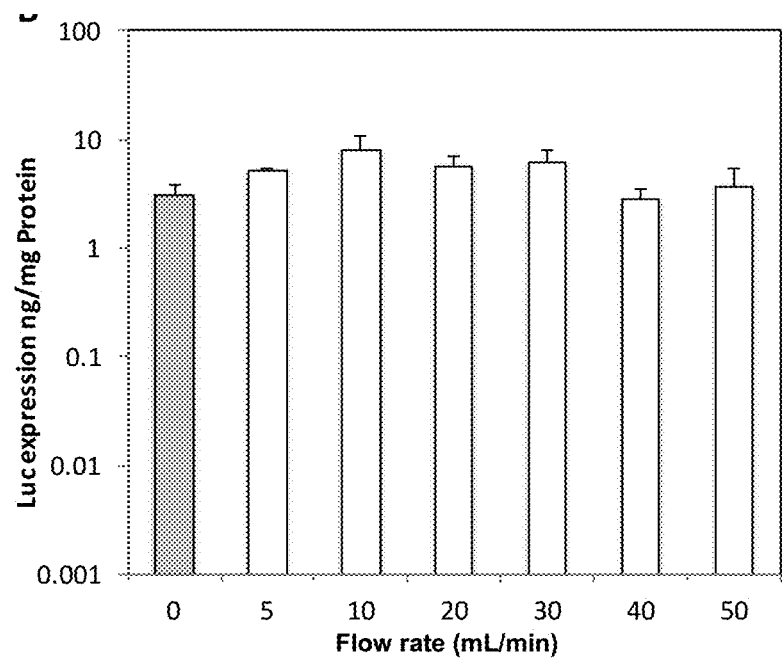
Figure 13:
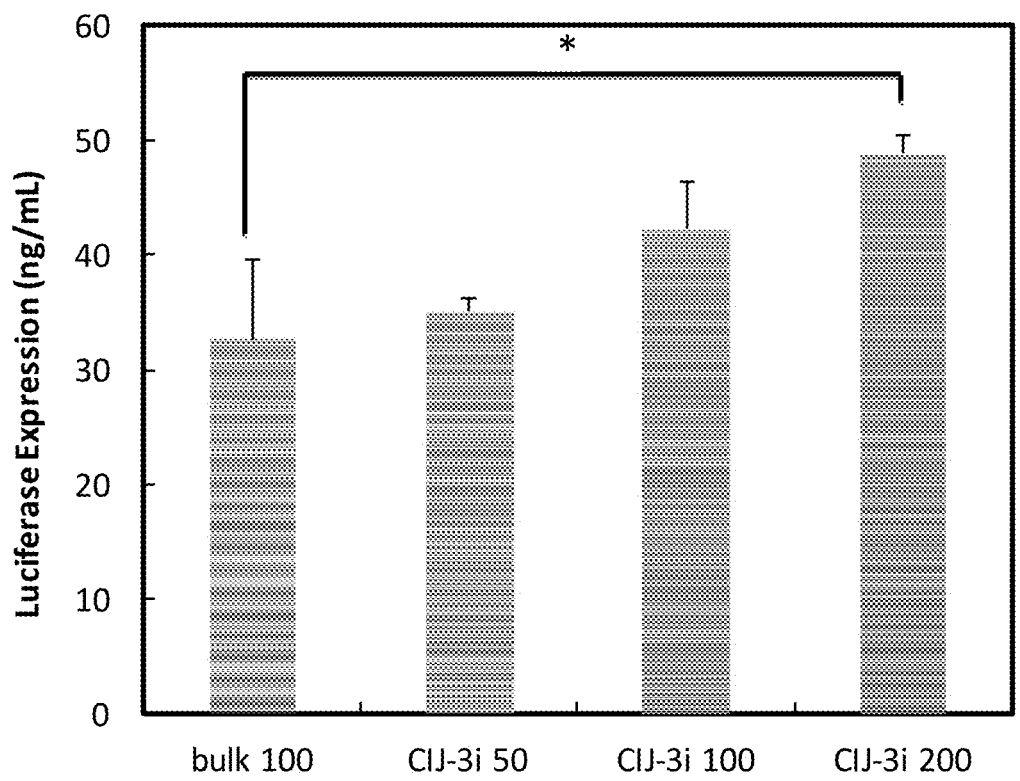
Figure 14A:
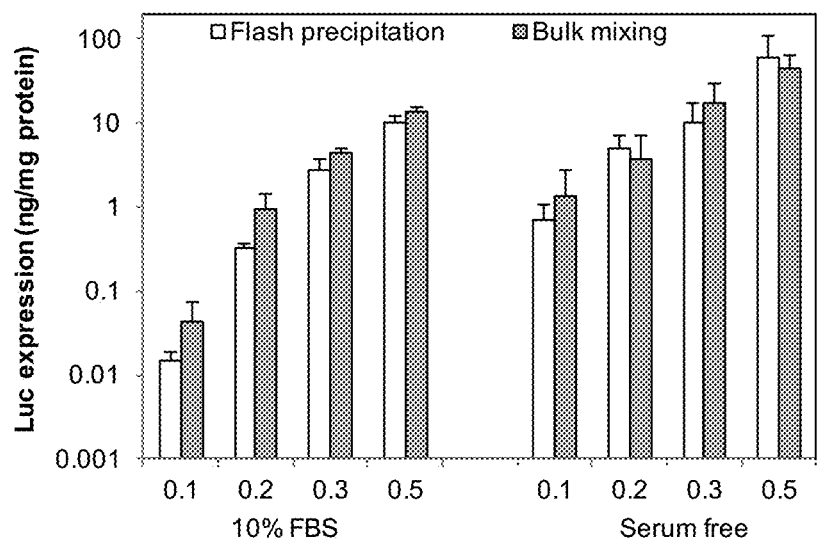
Figure 14B:
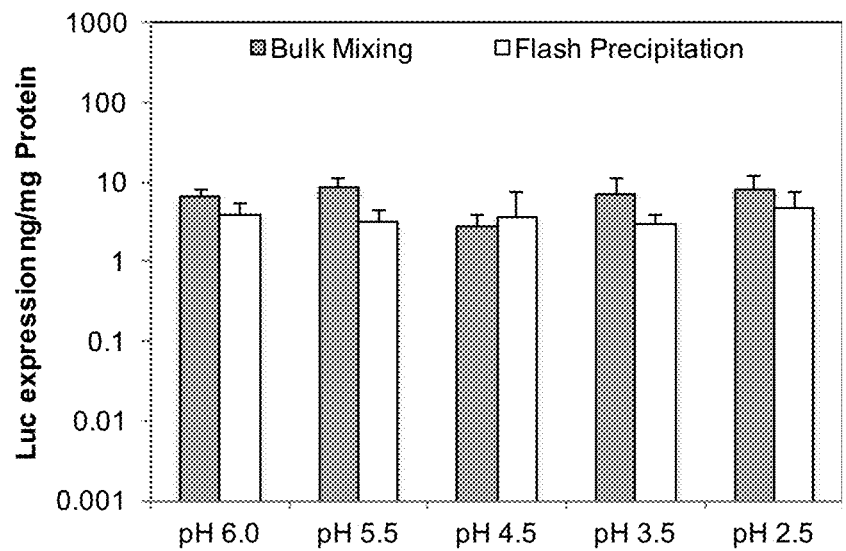
Figure 15:
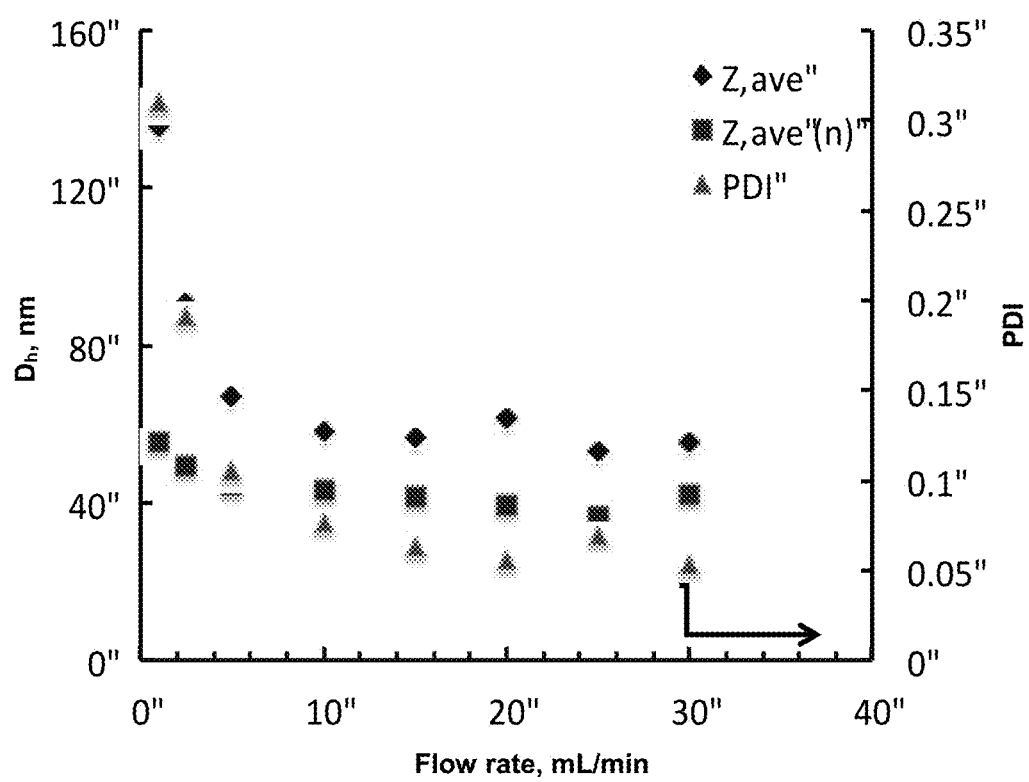
Figure 16A:
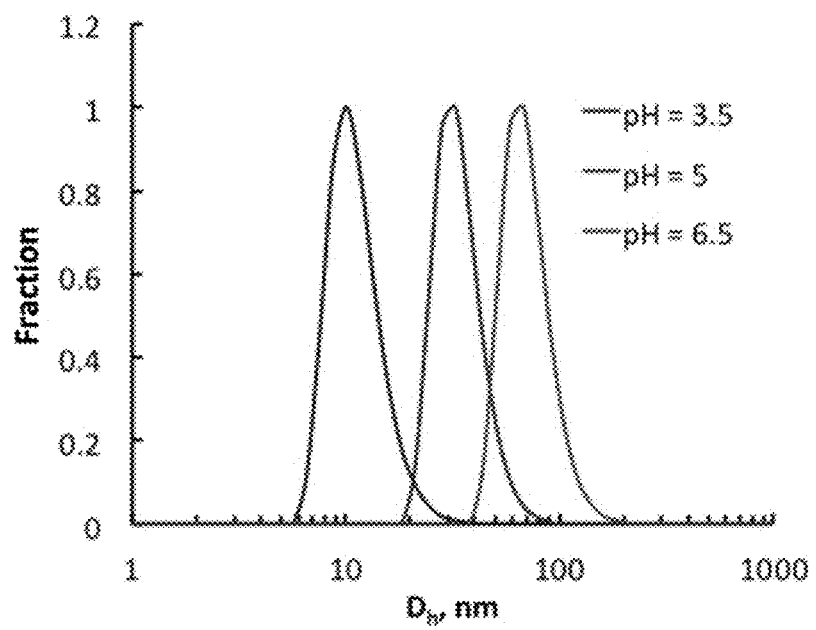
Figure 16B:
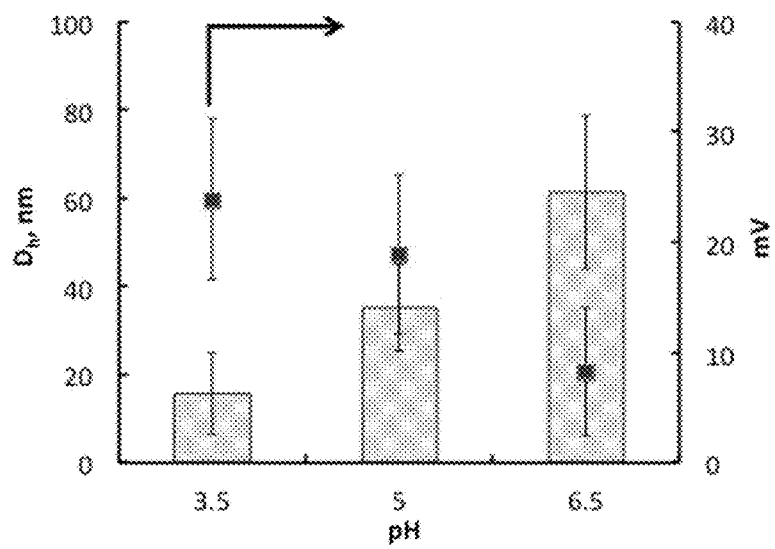
Figure 16C:
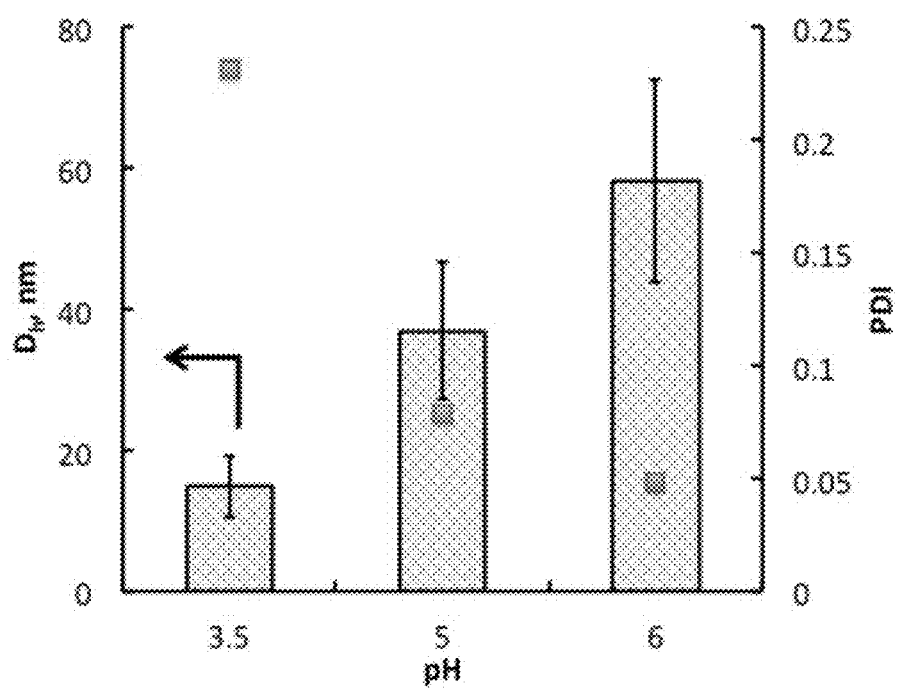
Figures 17A, 17B, 17C:
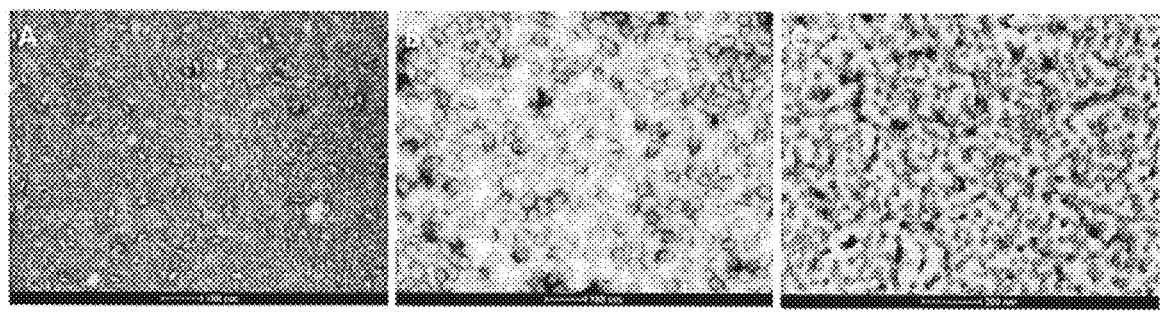
Figure 18A:
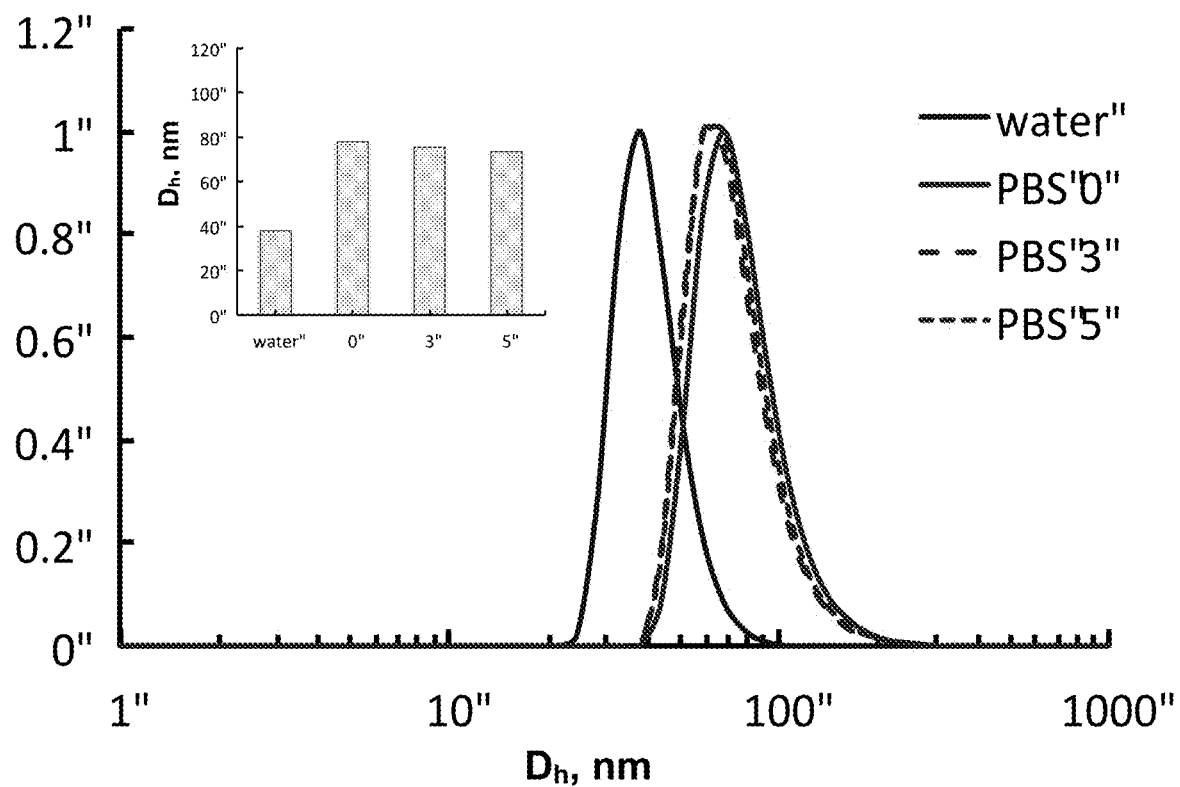
Figure 18B:
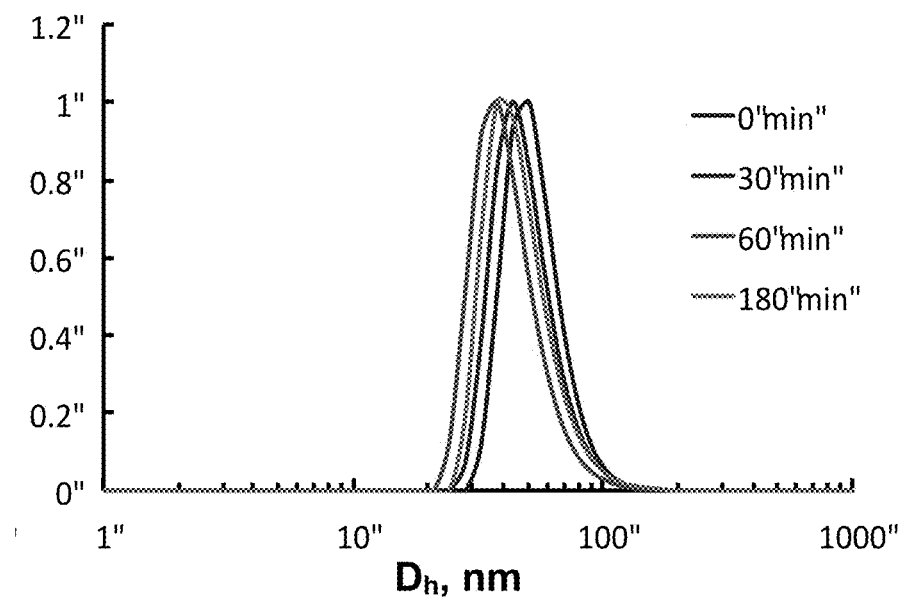
Figures 18C, 18D, 18E:
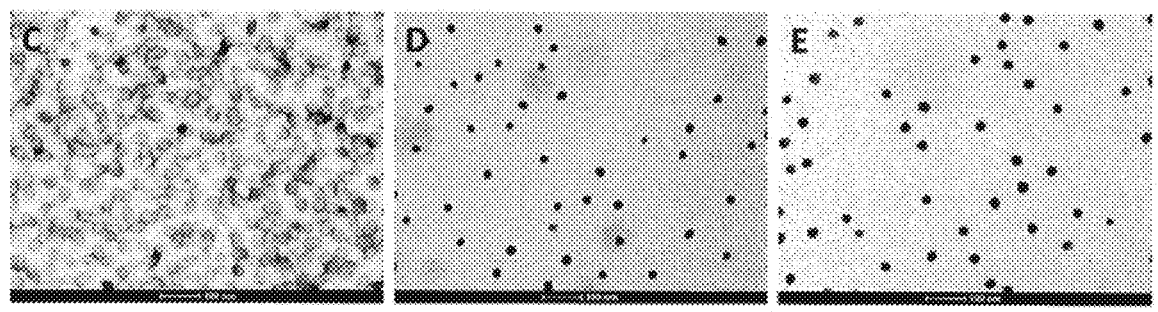
Figure 19A:
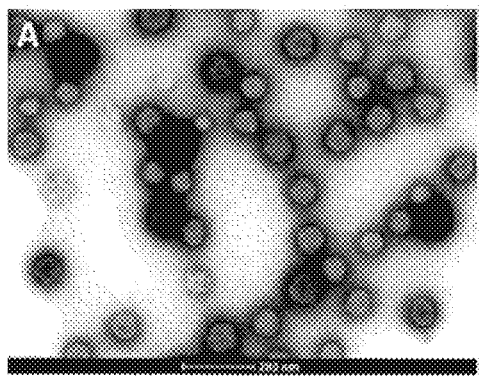
Figure 19B:
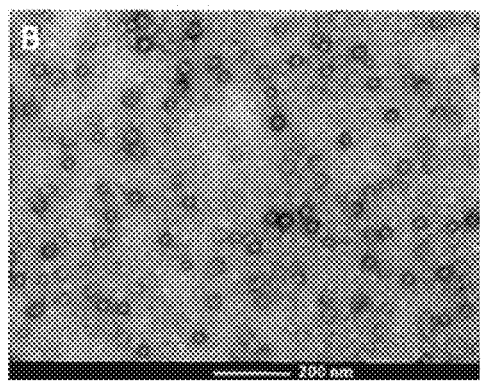
Figure 19C:
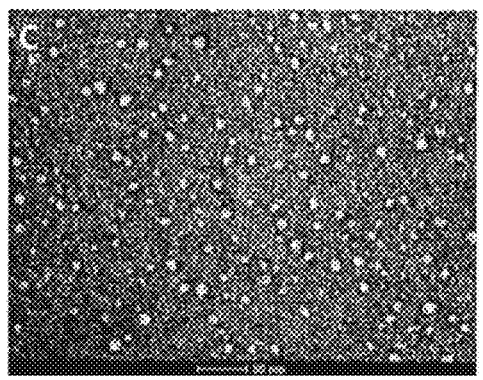
Figure 19D:
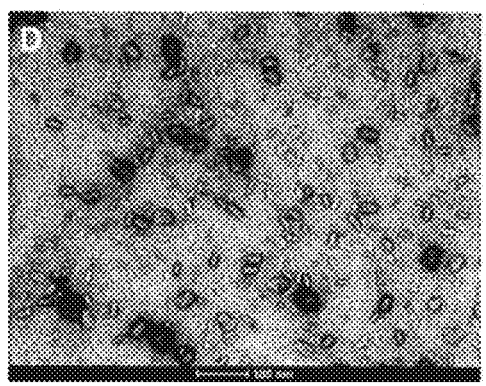

FIG. 9B shows zeta-potential of /PEI-DNA complex nanoparticles prepared under fast and bulk mixing, and polymer solutions of several pH values. DNA concentration was 25 µg/mL and N/P ratio 8;

FIG. 10 depicts an agarose gel electrophoresis image of bare plasmid DNA flowed through the CIJ mixer at various flow rates. Lane 1 represents standard DNA, and lanes 2 to 7 corresponds to DNA flowed through CIJ at a flow rate of 5, 10, 20, 30, 40 and 50 mL/min, respectively;

FIG. 11 depicts agarose gel electrophoresis of bare DNA (gel lanes nos. 2 and 4) and /PEI22 kDa:DNA nanoparticles (gel lanes nos. 3 and 5) formulations prepared using the CIJ-3i device at 2.5 (gel lane nos. 2 and 3) and 35 mL/min (gel lane nos. 3 and 5). Lane 1 represents standard DNA;

FIG. 12A and FIG. 12B depict in-vitro transfection efficiency of (FIG. 12A) jetPEI DNA and (FIG. 12B) Lipofectamine nanoparticles in HeLa cells. DNA was flowed through the CIJ at several flow rates and further complexed (bulk mixing) with either jetPEI or Lipofectamine, and compared to DNA that was not exposed to flow. Each bar represents mean±standard deviation (n=3);

FIG. 13 depicts in-vitro transfection of HeLa cells 48 hours following treatment of /PEI22 kDa:DNA nanoparticles prepared by bulk mixing (bulk 100 µg/ml DNA) and under rapid and homogeneous mixing in a CIJ-3i. 50, 100 and 200 is the concentration in µg/mL of DNA used for complexation (* indicates statistical significance with a p value <0.05, student t-test);

FIG. 14A and FIG. 14B depict in-vitro transfection efficiency of /PEI-DNA complex nanoparticles HeLa cells. FIG. 14A shows DNA-dose dependent transfection efficiency of /PEI-DNA complex nanoparticles generated under fast and bulk mixing conditions in 10% serum and serum free conditions. FIG. 14B shows transfection efficiency of /PEI-DNA complex nanoparticles generated under fast and bulk mixing conditions, and prepared with /PEI polymer solutions at different pH values. DNA concentration was 25 µg/mL and N/P ratio 8. Flow rate was 20 mL/min. Each bar represents mean±standard deviation (n=4);

FIG. 15 depicts the effect of flow rate on the average size and polydispersity of chitosan nanoparticles. Chitosan was dissolved in acetic acid 0.5% v/v, and the final pH was adjusted to 5.0 using a concentrated solution of sodium hydroxide before nanoparticle formulation;

FIG. 16A, FIG. 16B, and FIG. 16C depict number average particle size of chitosan:TPP nanoparticles prepared under dynamic conditions (FIG. 16A), effect of pH on particle size and zeta potential (FIG. 16B), and polydispersity (PDI, FIG. 16C) of chitosan:TPP nanoparticles;

FIG. 17A, FIG. 17B, and FIG. 17C depict TEM images of chitosan:TPP nanoparticles of various sizes prepared under rapid mixing conditions using a CIJ-3i device and chitosan solutions at different pH values. FIG. 17A, $pH_{chitosan}=3.5$; FIG. 17B, $pH_{chitosan}=5.0$; and FIG. 17C, $pH_{chitosan}=6.5$;

FIG. 18A, FIG. 18B, FIG. 18C, FIG. 18D, and FIG. 18E depict stability of chitosan:TPP nanoparticles in relevant biological medium. FIG. 18A shows stability in PBS 10 mM over 5 days, inset shows number average particle size in PBS; and FIG. 18B shows stability in FBS 2% v/v over 3 hours. Also shown are TEM images of chitosan:TPP nanoparticles in water (FIG. 18C), PBS after 3 days (FIG. 18D), and PBS after 5 days (FIG. 18E);

FIG. 19A, FIG. 19B, FIG. 19C, and FIG. 19D depict a formulation of several polyelectrolyte nanoparticles using a CIJ-3i device. FIG. 19A shows Chitosan:$Glu_5$ nanoparticles, FIG. 19B shows Chitosan-g-$PEG_{750}$:$Glu_5$, FIG. 19C shows Protamine sulfate:Heparin sulfate, and FIG. 19D shows Chitosan:poly(aspartic acid sodium salt);

FIG. 20A, FIG. 20B, FIG. 20C, FIG. 20D, and FIG. 20E depict encapsulation of bovine serum albumin (BSA) m chitosan:TPP nanoparticles using dynamic conditions.

Figure 20A:
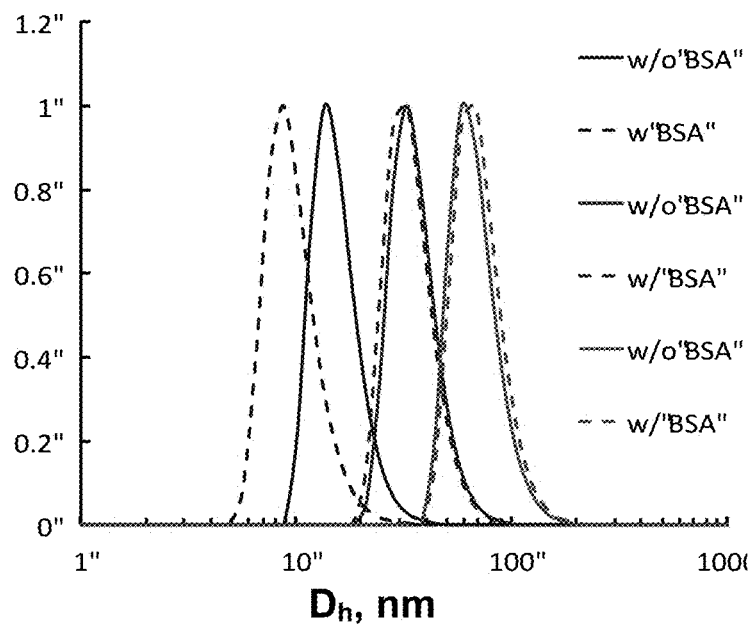
Figure 20B:
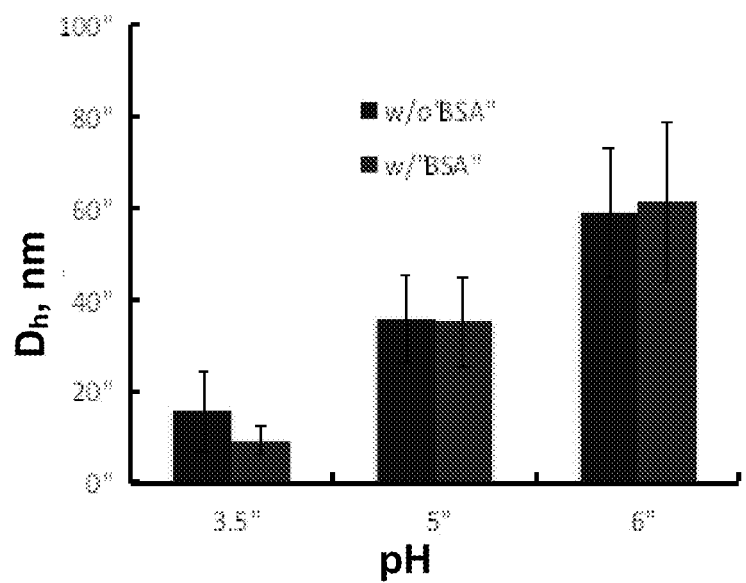
Figure 20C:
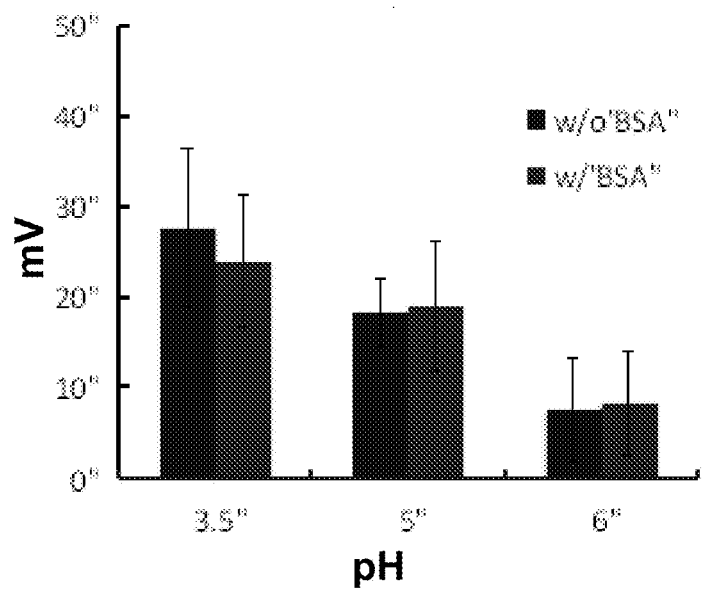
Figure 20D:
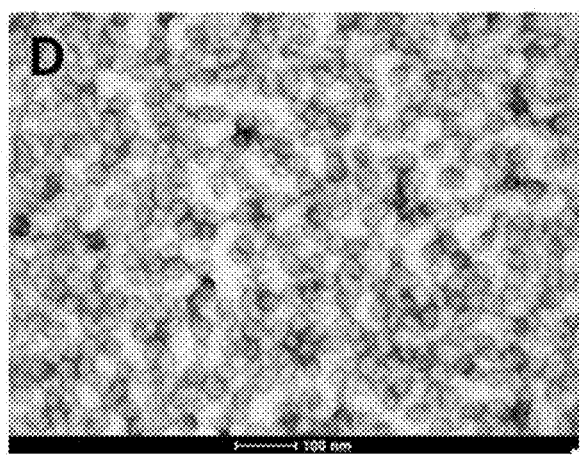
Figure 20E:
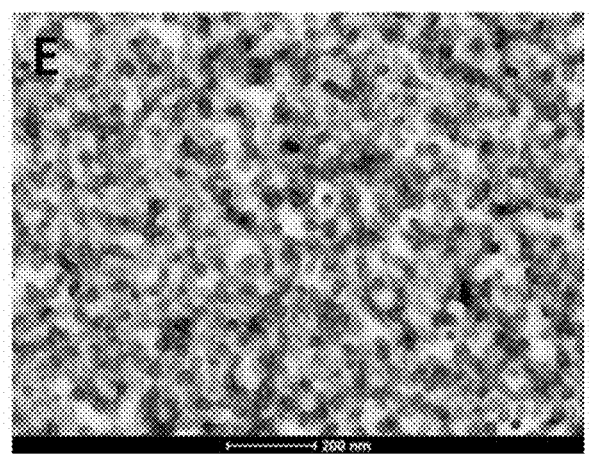
Figure 21:
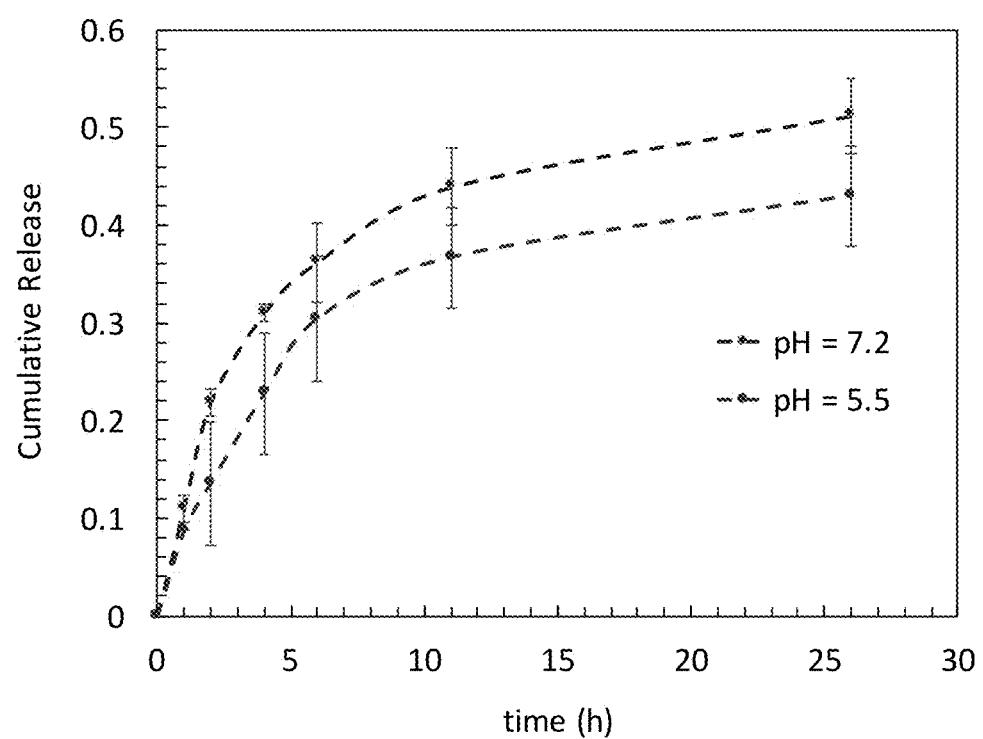

FIG. 20A shows number average size distribution for empty or BSA-encapsulating nanoparticles prepared at different pH values; blue lines: pH 3.5, red lines: pH 5.0, and green lines: pH 6.0. FIG. 20B shows number average particle size of empty or BSA-encapsulating nanoparticles, FIG. 20C shows zeta potential of empty or BSA-encapsulating nanoparticles, FIG. 20D shows TEM images of empty nanoparticles, and FIG. 20E shows TEM images of BSA-encapsulating nanoparticles. BSA was encapsulated at an initial concentration of 0.25 mg/mL. Chitosan and TPP concentrations were 0.5 mg/mL and 0.25 mg/mL, respectively; and FIG. 21 depicts an in-vitro cumulative release profile of BSA from chitosan:TPP nanoparticles in PBS at 37° C. The nanoparticles were prepared at 20 mL/min flow rate using rhodamine-labeled BSA (initial concentration of 0.1 mg/mL). Chitosan (pH 5.0) and TPP concentrations were 0.5 mg/mL and 0.25 mg/mL, respectively.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides a new method, flash nanocomplexation (FNC), which is capable of producing polyelectrolyte complex nanoparticles in a continuous and scalable manner. FNC generates nanoparticles as a result of polyelectrolyte complexation without relying on solvent-induced supersaturation of copolymers. It is believed that disclosed herein is the first example of FNC for the preparation of polyelectrolyte complex nanoparticles. Also provided are compositions produced from FNC and a device for preparing the compositions.

The polyelectrolyte complex nanoparticles produced by FNC have a smaller size, better uniformity and lower polydispersity than polyelectrolyte complexes prepared using conventional methods. For example, compared to bulk preparation methods, the FNC process allows for the formation of uniform aggregates with tunable size in a continuous flow operation process, which is amenable for scale-up production. FNC also offers a higher degree of versatility and control over particle size and distribution, higher drug encapsulation efficiency, and improved colloidal stability (Shen et al., 2011; D'Addio et al., 2013; D'Addio et al., 2102; Gindy et al., 2008; Lewis et al., 2015; D'Addio et al., 2011; Luo et al., 2014; Santos et al., 2014).

Furthermore, the presently disclosed methods result in condensed and compact polyelectrolyte nanoparticles through improved polymer chain entanglement. In addition, the methods provide a means to efficiently encapsulate therapeutic agents, such as proteins or nucleic acids, in polyelectrolyte nanoparticles while retaining their intrinsic physiochemical properties. Furthermore, formulations of DNA-containing nanoparticles prepared with these novel methods have improved particle size and shape distribution, and exhibit higher cell transfection efficiency when compared to bulk preparation methods.

I. Methods of Preparing Polyelectrolyte Complex Nanoparticles

In some embodiments, the presently disclosed subject matter provides a flash nanocomplexation (FNC) method of continuously generating uniform polyelectrolyte complex (PEC) nanoparticles, the method comprising: (a) flowing a first stream comprising one or more water-soluble polycationic polymers at a first variable flow rate into a confined chamber; (b) flowing a second stream comprising one or more water-soluble polyanionic polymers at a second variable flow rate into the confined chamber; and (c) impinging the first stream and the second stream in the confined chamber until the Reynolds number is from about 1,000 to about 20,000, thereby causing the one or more water-soluble polycationic polymers and the one or more water-soluble polyanionic polymers to undergo a polyelectrolyte complexation process that continuously generates PEC nanoparticles.

In some embodiments, the presently disclosed subject matter is directed to a method of forming polyelectrolyte complex nanoparticles. As used herein "polyelectrolyte complexes" (also known as polyelectrolyte coacervates or "PECs") are the association complexes formed between oppositely charged particles (e.g., polymer-polymer, polymer-drug, and polymer-drug-polymer). Polyelectrolyte complexes are formed due to electrostatic interaction between oppositely charged polyions, i.e. water-soluble polycations and water-soluble polyanions. As used herein, the term "continuously" refers to a process that is uninterrupted in time, such as the generation of PEC nanoparticles while at least two presently disclosed streams are flowing into a confined chamber. As used herein, the term "water-soluble" refers to the ability of a compound to be able to be dissolved in water.

In some embodiments, the water-soluble polyions are dissolved in a suitable solvent, resulting in elementary charges distributed along the macromolecular chains. In various embodiments, polyelectrolyte complexes are formed when macromolecules of opposite charge are allowed to interact. For example, in some embodiments, flash precipitated nanoparticles of polyelectrolyte complexes are formed by rapidly and homogenously mixing streams, i.e., a water-soluble polycation dissolved in a stream and a water-soluble polyanion dissolved in a stream.

In some embodiments, the streams are compositions that include one or more fluid components and are capable of carrying a solid or solids in solution or suspension. Typically, the streams are polar, e.g. acetic acid or water. More typically, the stream is water.

The streams are impinged in the confined chamber until the Reynolds number is from about 1,000 to about 20,000, thereby causing the water-soluble polycationic polymers and the water-soluble polyanionic polymers to undergo a polyelectrolyte complexation process that continuously generates PEC nanoparticles. As used herein, the term "impinging" refers to at least two streams striking each other in the confined chamber at a high flow rate. Using the presently disclosed methods and device, it has been surprisingly shown that a molecule, such as a DNA molecule, remains intact under such high shear conditions.

The rapid and homogenous mixing of the first and second streams to generate polyelectrolyte complex nanoparticles, for example, can be achieved through various methods during which the flow rate and the mixing efficiency and velocity is controlled. In some embodiments, polyelectrolyte complex nanoparticles may be produced by flash nanocomplexation using a centripetal mixer or a batch flash mixer. See, for example, Johnson et al., U.S. Patent Application Publication No. 2004/0091546, which is herein incorporated by reference in its entirety.

As another example, the mixing of the first and second streams may be accomplished using a confined impinging jet (CIJ) device with at least two high-velocity jets (FIG. 1A, FIG. 1B, FIG. 1C, FIG. 1D, and FIG. 1E). In a typical embodiment, oppositely charged streams are loaded into separated syringes and fed into a confined chamber of a CIJ device by digitally controlled syringe pumps (e.g., New Era Pump System, model NE-4000). In some embodiments, a long tube runner serving as an outlet is used to ensure that the opposing streams brought into the confined chamber are fully reacted before collection. In some embodiments, the first stream and the second stream are on opposing sides when entering the confined chamber. As used herein, the term "opposing sides" means that the streams are generally opposite each other. In some embodiments, the streams are directly opposite each other. In some embodiments, the streams may not be directly opposite each other.

Methods of the present disclosure also include providing one or more additional streams. For example, in some embodiments, the method could include providing a third stream comprising a further additive such as a therapeutic agent as described herein below, a saline solution, a water miscible organic solvent (e.g., dimethyl sulfoxide, dimethyl formamide, acetonitrile, tetrahydrofuran, methanol, ethanol, isopropanol), to control the polarity of the final formulation in situ, or a cryoprotectant (e.g., glycerol, trehalose, sucrose, dextrose) to improve the colloidal stability of the nanoparticles upon reconstitution. In some embodiments, a third, fourth or even further numbers of jets may be added to a CIJ device to accommodate additional streams with additives such as those described herein.

In some embodiments, the presently disclosed methods further comprise flowing a third stream into the confined chamber, wherein each stream is equidistant from the other two streams when entering the confined chamber. In some embodiments, keeping the streams equidistant from each other allows even mixing of the streams to occur.

In some embodiments, the pH value of the first stream and the pH value of the second stream range from about 2.5 to about 8.4. In some embodiments, the pH value of the first stream and the pH value of the second stream range from about 3.5 to about 7.4.

The flow rate at which the streams contained in the syringes of the above described CIJ device may be impinged into the confined chamber may be readily tuned via the programmable syringe pumps, for example. Further, in some embodiments, the characteristic mixing time is a function of the flow rate and can be adjusted by changing the flow rate. For instance, at high flow rates, the flow pattern may assume turbulent-like characteristics and the mixing time may be in the order of a few milliseconds. Under these conditions, efficient mass transfer is achieved, and discrete and uniform nanoparticles with a narrow size distribution may be produced. In various embodiments, the final average particle size is a function of the mixing time, the concentration and the chemical composition of the polyelectrolytes.

The mixing efficiency and the nature of the flow, which influence the mixing velocity, is commonly defined by the Reynold's number (Re), a dimensionless number representing the ratio of the inertial flow to the viscous force. For a CIJ device, the collective Re numbers is calculated by accumulating the contribution of multiple streams:

$$\text{Re} = \sum_{i=1}^{n} \text{Re}_i = \frac{4}{\pi d} \sum_{i=1}^{n} \frac{\rho_i Q_i}{\mu_i}$$

whereas $\rho_i$ is the density of the solution in the ith inlet stream (kg/m$^3$); $Q_i$ is the flow rate of the ith inlet stream (m$^3$/s); $\mu_i$ is the fluid viscosity of the ith inlet stream (Pa s); $d_i$ is the diameter of the ith inlet nozzle (m) and n is the number of streams.

In some embodiments, the Reynold's number achieved during mixing of the reactants is about 1,000 to about 20,000, such as about 1,600 to about 10,000, about 2,000 to about 10,000, about 2,000 to about 8,000, about 1,900 to about 5,000, and about 3,000 to about 5,000.

In some embodiments, the variable flow rates of the streams range from about 1 milliliter (mm)/minute to about 50 mm/minute, such as between about 5 mm/minute to about 40 mm/minute, and between about 20 mm/minute to about 30 mm/minute. In some embodiments, the variable flow rates of the streams are greater than about 5 mm/minute. In some embodiments, the ratio of the flow rate of the second stream to the flow rate of the first stream is from about 0.1 to about 10.

In some embodiments, an additive is included within a stream. For example, a therapeutic agent may be added to either a stream containing a water-soluble polycation and/or a second stream containing a water-soluble polyanion. In some embodiments, the first stream and/or the second stream further comprise one or more water-soluble therapeutic agents. In some embodiments, the generated PEC nanoparticles encapsulate at least one or more water-soluble therapeutic agents.

In some embodiments, one or more water-soluble therapeutic agents are selected from the group consisting of small molecules, such as small organic or inorganic molecules; saccharides; oligosaccharides; polysaccharides; a biological macromolecule selected from the group consisting of peptides, proteins, peptide analogs and derivatives; peptidomimetics; nucleic acids, such as DNA, RNA interference molecules, selected from the group consisting of siRNAs, shRNAs, antisense RNAs, miRNAs and ribozymes, dendrimers and aptamers; antibodies, including antibody fragments and intrabodies; an extract made from biological materials selected from the group consisting of bacteria, plants, fungi, animal cells, and animal tissues; naturally occurring or synthetic compositions; and any combination thereof. In some embodiments, one or more water-soluble therapeutic agents are selected from the group consisting of a small molecule, carbohydrate, sugar, protein, peptide, nucleic acid, antibody or antibody fragment thereof, hormone, hormone receptor, receptor ligand, cytokine, and growth factor.

In some embodiments, one or more water-soluble polycationic polymers are selected from the group consisting of chitosan, PAMAM dendrimers, polyethylenimine (PEI), protamine, poly(arginine), poly(lysine), poly(beta-aminoesters), cationic peptides and derivatives thereof.

In some embodiments, one or more water-soluble polyanionic polymers are selected from the group consisting of poly(aspartic acid), poly(glutamic acid), negatively charged block copolymers (poly(ethylene glycol)-b-poly(acrylic acid), poly(ethylene glycol)-b-Poly(aspartic acid), poly(ethylene glycol)-b-poly(glutamic acid), heparin sulfate, dextran sulfate, hyaluronic acid, alginate, tripolyphosphate (TPP), poly(glutamic acid), a cytokine (e.g., a chemokine, interferon, interleukin, lymphokine, tumor necrosis factor), a protein, a peptide, a growth factor, and a nucleic acid.

The terms "polypeptide" and "protein" as used herein refer to a polymer of amino acids. As used herein, a "peptide" refers to short chain of amino acid monomers, such as about 50 or fewer amino acids.

As used herein, a "growth factor" refers to a substance, such as a protein or hormone, which is capable of stimulating cellular growth, proliferation, healing, and/or cellular differentiation. Non-limiting examples of growth factors include platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), and bone morphogenetic factors.

As used herein, a "nucleic acid" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes.

In some embodiments, the nucleic acid is an RNA interfering agent. As used herein, an "RNA interfering agent" is defined as any agent that interferes with or inhibits expression of a target gene, e.g., by RNA interference (RNAi). Such RNA interfering agents include, but are not limited to, antisense molecules, ribozymes, small inhibitory nucleic acid sequences, for example but not limited to guide RNAs, small interfering RNA (siRNA), short hairpin RNA or small hairpin RNA (shRNA), microRNA (miRNA), post-transcriptional gene silencing RNA (ptgsRNA), short interfering oligonucleotides, antisense oligonucleotides, aptamers, CRISPR RNAs, nucleic acid molecules including RNA molecules which are homologous to the target gene, or a fragment thereof, and any molecule which interferes with or inhibits expression of a target gene by RNA interference (RNAi).

In some embodiments, the nucleic acid is selected from the group consisting of an antisense oligonucleotide, cDNA, genomic DNA, guide RNA, plasmid DNA, vector DNA, mRNA, miRNA, piRNA, shRNA, and siRNA. In some embodiments, the nucleic acid is not siRNA. As used herein, the term "plasmid DNA" refers to a small DNA molecule that is typically circular and is capable of replicating independently.

In some embodiments, one or more water-soluble polyanionic polymers is plasmid DNA and one or more water-soluble polycationic polymers is selected from the group consisting of linear polyethylenimine (PEI) and its derivatives, such as but not limited to, poly(ethylene glycol)-b-PEI and poly(ethylene glycol)-g-PEI.

In some embodiments, the second stream comprises one or more water-soluble therapeutic agents and the polyelectrolyte complexation process encapsulates one or more water-soluble therapeutic agents in the generated polyelectrolyte complex (PEC) nanoparticles.

In some embodiments, the polyelectrolyte complex nanoparticles comprise polycations and polyanions such as chitosan/TPP, protamine/heparin sulfate, PEI/DNA, chitosan-g-PEG17/Glu5, chitosan/poly-aspartic acid sodium salt and protamine sulfate/heparin. In some embodiments, the first stream comprises chitosan and the second stream comprises tripolyphosphate (TPP) and a protein, wherein the protein is co-encapsulated by the TPP and chitosan in the generated polyelectrolyte complex (PEC) nanoparticles.

The concentrations of the polycation and polyanion will depend upon the specific macromolecules used and the desired shape and uniformity of the resulting polyelectrolyte complex nanoparticles. Specific embodiments are described in the Examples below.

In some embodiments, increasing the concentration of the water-soluble polycation and/or water-soluble polyanion and/or increasing the pH of a stream can affect the shape, particle size and/or particle size uniformity. For example, when the concentration of a stream containing DNA is increased, while the concentration of a water-soluble polycation such as PEI remains constant, the shape of the resultant nanoparticles formed during flash nanocomplexation may, in some embodiments, be generally more rod-like rather than spherical. Further, increasing the pH of either the water-soluble polycation and/or water-soluble polyanionic streams can also result in more rod-like shaped nanoparticles. Conversely, spherically shaped nanoparticles may generally be obtained in some embodiments, by increasing the concentration and/or pH of the water-soluble polycation and/or water-soluble polyanion streams.

As described herein, in some embodiments, the stream will contain an additive such as a therapeutic agent, for example, a water-soluble therapeutic agent. For example, a water-soluble therapeutic agent, such as a protein, may be added to a stream containing a water-soluble polyanion, such as TPP. The water-soluble polyanionic stream containing the protein and the water-soluble polycationic stream containing chitosan, for example, may be independently loaded into a syringe of a CU device to obtain protein-containing nanoparticles co-encapsulated by the chitosan and the TPP.

In some embodiments, a water-soluble therapeutic agent such as a nucleic acid, e.g. siRNA, may complexed with, for example, a water-soluble polycation such as PEI in a nanoparticle. Accordingly, a water-soluble polyanion of the present disclosure may be used to both form the instant polyelectrolyte complex nanoparticle described herein and to act as a therapeutic agent.

II. Polyelectrolyte Complex Nanoparticles

In some embodiments, the presently disclosed subject matter provides a uniform polyelectrolyte complex (PEC) nanoparticle preparation generated from a flash nanocomplexation (FNC) method, the method comprising: flowing a first stream comprising one or more water-soluble polycationic polymers at a first variable flow rate into a confined chamber; flowing a second stream comprising one or more water-soluble polyanionic polymers at a second variable flow rate into the confined chamber; and impinging the first stream and the second stream in the confined chamber until the Reynolds number is from about 1,000 to about 20,000, thereby causing the one or more water-soluble polycationic polymers and the one or more water-soluble polyanionic polymers to undergo a polyelectrolyte complexation process that continuously generates PEC nanoparticles.

The presently disclosed uniform polyelectrolyte complex nanoparticles have particle sizes, distributions of particle sizes, and polyanion and polycation components as described above and in the Examples below. In some embodiments, the uniform polyelectrolyte complex nanoparticles of the present disclosure encapsulate one or more additives, as described herein, such as water-soluble therapeutic agents.

In some embodiments, the polyelectrolyte complex nanoparticles, which are formed according to the present methods are uniform in particle size, i.e., there is a narrow distribution of particle size. For example, in some embodiments, the present nanoparticles have an average particle size of less than about 500 nm, less than about 100 nm, less than about 60 nm, or less than about 40 nm (homogenous diameter). In some embodiments, the generated polyelectrolyte complex nanoparticles range in size from about 20 nm to about 500 nm in diameter. In some embodiments, the generated polyelectrolyte complex nanoparticles range in size from about 25 nm to about 100 nm in diameter. In some embodiments, the generated polyelectrolyte complex nanoparticles range in size from about 30 nm to about 80 nm in diameter. In some embodiments, the generated polyelectrolyte complex nanoparticles range in size from about 25 nm to about 60 nm in diameter. In some embodiments, the generated polyelectrolyte complex nanoparticles range in size from about 30 nm to about 45 nm in diameter. In some embodiments, the generated polyelectrolyte complex nanoparticles are about 30 nm in diameter.

In some embodiments, the polydispersity index (PDI) of the generated polyelectrolyte complex nanoparticles may range from about 0.05 to about 0.2, more typically about 0.05 to 0.1, even more typically about 0.05. Generally, the lower the PDI, the lower the distribution of particle size in a nanoparticle population. In some embodiments, the polydispersity index of the generated polyelectrolyte complex (PEC) nanoparticles ranges from about 0.05 to about 0.1. In some embodiments, the polydispersity index of the generated polyelectrolyte complex nanoparticles is about 0.05.

III. Device for Preparing Polyelectrolyte Complex Nanoparticles

The presently disclosed subject matter also provides a device for continuously generating uniform polyelectrolyte complex (PEC) nanoparticles, the device comprising: (a) a housing comprising: (i) a confined chamber; (ii) a first inlet configured to permit a first stream comprising one or more water-soluble polycationic polymers to flow into the confined chamber; (iii) a second inlet configured to permit a second stream comprising one or more water-soluble polyanionic polymers to flow into the confined chamber; and (iv) optionally a third inlet configured to permit a third stream to flow into the confined chamber; (b) a first conduit providing a first stream path configured to permit the first stream to flow into the confined chamber at a first variable flow rate through the first inlet, wherein the first conduit has a first variable diameter; (c) a second conduit providing a second stream path configured to permit the second stream to flow into the confined chamber at a second variable flow rate through the second inlet, wherein the second conduit has a second variable diameter; and (d) optionally a third conduit providing a third stream path configured to permit the third stream to flow into the confined chamber at a third variable flow rate through the third inlet, wherein the third conduit has a third variable diameter; wherein the first conduit, the second conduit, and the third conduit if present, are situated equidistantly relative to each other on an exterior surface of the housing in a manner that permits impinging of the streams in the confined chamber until the Reynolds number is from about 1,000 to about 20,000, thereby causing the one or more water-soluble polycationic polymers and the one or more water-soluble polyanionic polymers to undergo a polyelectrolyte complexation process that continuously generates PEC nanoparticles.

In some embodiments, the housing may be produced from a variety of materials, such as high-density polyethylene, polyoxymethylene, polytetrafluoroethylene, and/or stainless steel, as long as the material allows the formation of a confined chamber and paths for the insertion of conduits within the housing. In some embodiments, the housing may be a variety of shapes, such as including, but not limited to, a spheroid, a rectangular cuboid, a pyramid, a cube, and a cylinder. In some embodiments, the housing is in the shape of a circular cylinder.

In some embodiments, the conduits extend from the exterior of the housing, into the inlet, and to the confined chamber. In some embodiments, the conduits are permanently affixed to the corresponding inlet. In some embodiments, the conduits are connected to an inlet in a removable manner. In some embodiments, the lengths of the conduits vary depending on the size of the housing and confined chamber. In some embodiments, the conduits comprise polyethylene (PE), polypropylene (PP), polytetrafluoroethylene (PTFE), polyether ether ketone (PEEK), or stainless steel.

Impinging of the streams to generate the PEC nanoparticles occurs in the confined chamber. In some embodiments, the confined chamber is any shape that allows the streams to enter into the confined chamber equidistant from each other. In some embodiments, the confined chamber is a circular cylinder. In some embodiments, the confined chamber ranges in diameter from about 0.5 millimeters (mm) to about 10 mm. In some embodiments, the confined chamber is a circular cylinder ranging in diameter from about 1.0 mm to about 7.5 mm. In some embodiments, the confined chamber is a circular cylinder ranging in diameter from about 1.25 mm to about 7.5 mm. In some embodiments, the confined chamber is a circular cylinder ranging in diameter from about 1.25 mm to about 5.0 mm. In some embodiments, the confined chamber is a circular cylinder ranging in height from about 2.5 mm to about 15 mm.

In some embodiments, the impinged streams comprise a mixed solution containing the generated PEC nanoparticles, and the housing further comprises at least one outlet configured to remove the mixed solution containing the generated PEC nanoparticles from the device after impinging of the streams occurs in the confined chamber.

In some embodiments, two streams are introduced into the device through independent inlet tubes having an inner diameter of about 0.2 mm to about 6 mm, typically about 0.25 mm to about 3.0 mm in diameter for laboratory scale production. The device may include temperature control elements to adjust the temperature of fluid in the inlet tubes and in the confined chamber. The PEC nanoparticles may be collected in scintillation vials through PTFE tubing, for example, (ID=about 0.75 mm), having a length, e.g. 12.7 cm, sufficient to ensure complete mixing of components in the confined chamber.

Representative embodiments of the presently disclosed device are shown in FIG. 1B, FIG. 1C, FIG. 1D, and FIG. 1E. As seen in FIG. 1C, in some embodiments, diameter d1 ranges from about 0.25 mm to about 1.5 mm, such as from about 0.3 mm to about 1.0 mm, and from about 0.4 mm to about 0.8 mm. As seen in FIG. 1C, in some embodiments, diameter d3 is equal to about 0.5 of diameter d1, diameter d2 is equal to about two times diameter d1, and diameter D (output channel) is equal to about five times diameter d1. In some embodiments, D=2.5 mm, d1=0.5 mm, d2=1.0 mm, d3=0.25 mm, H=0.9D, Z=1.3D, and Q=6.35 mm. In some embodiments, diameter Q can vary and other diameters are not dependent on diameter Q.

In some embodiments, the first conduit, the second conduit, and the third conduit if present each have a first section with a diameter d2 in fluid communication with a second section with a diameter d1 in fluid communication with the confined chamber, wherein the diameter d1 ranges from about 0.25 mm to about 1.5 mm and the ratio of the diameter d2 to the diameter d1 ranges from about 1.5 to about 3.0.

In some embodiments, the first conduit, the second conduit, and the third conduit if present each have a first section with a diameter d2 in fluid communication with a second section with a diameter d1 in fluid communication with the confined chamber, wherein the diameter d1 ranges from about 0.25 mm to about 1.5 mm and the ratio of the diameter d2 to the diameter d1 ranges from about 1.8 to about 2.5.

In some embodiments, the first conduit, the second conduit, and the third conduit if present each have a first section with a diameter d2 in fluid communication with a second section with a diameter d1 in fluid communication with the confined chamber, wherein the diameter d1 ranges from about 0.25 mm to about 1.5 mm and the ratio of the diameter d2 to the diameter d1 is about 2.0.

In some embodiments, the first conduit, the second conduit, and the third conduit if present each have a first section with a diameter d2 in fluid communication with a second section with a diameter d1 in fluid communication with the confined chamber, and wherein the first section and the second section are inside the housing and external to the confined chamber.

In some embodiments, the third conduit is present in the device. In some embodiments, the third conduit is present in the device and the stream path of the third conduit is blocked off.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

PEI/DNA Polyelectrolyte Complex Nanoparticles

Materials and Methods

Materials: WEI (linear polyethyleneimine, molecular weight 22 kDa) was a kind gift from Polymer Chemistry Innovations, Inc. (Tucson, Ariz.) and fractioned using Amicon centrifugal filter. Plasmid DNA, VR1255C (6.4 kb), encoding the gene for firefly luciferase driven by the cytomegalovirus promoter, was kindly provided by Vical (San Diego, Calif.). Plasmid DNA was amplified in DH5α *E. coli* and was purified using an EndoFree Giga Kit (Qiagen, Valencia, Calif.) and dissolved at 1 mg/mL in endotoxin-free TE buffer. Unless otherwise stated, all other chemicals were purchased from Sigma-Aldrich.

Nanoparticle Formation: 1PEI-DNA complex nanoparticles were prepared in a CIJ mixer equipped with two streams. The FNC process in a CIJ device are illustrated in FIG. 1A. The chamber dimensions are the same as those previously used in Johnson's and Liu's work and are represented in FIG. 1C (Johnson et al., 2003; Han et al., 2012, which are herein incorporated by reference in their entireties). It should be noted the mixer used herein is designed to allow unequal flow momentum from the two opposing jets, (Han et al., 2012; Zhu et al., 2014), which are herein incorporated by reference in their entireties. Typically, the mixer inlets are connected to gas-tight plastic syringes (5, 10, 20, and 50 mL) via ETFE tubing with an inner diameter (ID) of 1.55 mm. The complex nanoparticles are collected in scintillation vials through a PTFE tubing (ID=0.75 mm), whose length (12.7 cm) is enough to ensure complete mixing of components in the chamber. The flow rate at which the solutions of polymers and nucleic acids contained in syringes are impinged into the confined chamber is readily tuned via programmable syringe pumps (New Era Pump System, model NE-4000). The mixing efficiency and the nature of the flow is commonly defined by the Reynold's number (Re) as described above.

For a typical nanoparticle preparation, DNA was diluted in 2 mL of DI water to give a final concentration of 25- to 200 µg/mL DNA. A solution of /PEI was diluted to 2 mL in DI water to give a final N/P ratio (ratio of amine in /PEI to phosphate in DNA) of 8. Both solutions were loaded in separate syringes, and the two streams were impinged at varying flow rates (1 mL/min up to 50 mL/min) inside the mixing chamber. The complex nanoparticles were collected and promptly characterized by DLS, charge, TEM, and evaluated in terms of transfection efficiency using a cancer cell line.

Transmission Electron Microscopy:

TEM imaging of nanoparticles was done by incubating 10 µL of /PEI-g-PEG/DNA nanoparticle solution onto an ionized nickel grid covered with a carbon film. After 10 min, the solution was removed, and a 6-µL drop of 2% uranyl acetate was added to the grid. After 20 s, the staining solution was removed, and the grid was dried at room temperature. The samples were imaged with a Technai FEI-12 electron microscope. Nanoparticle sizes were characterized from TEM images using Image J 1.44.

Size and Zeta Potential Measurement:

Particle size and zeta potential were measured by photon correlation spectroscopy and laser Doppler anemometry, respectively, using a Zetasizer Nano ZS90 (Malvern Instruments, Southborough, Mass.). Size measurement was performed at 25° C. at a 90° scattering angle. The mean hydrodynamic diameter was determined by cumulative analysis. The zeta potential measurements were performed using a DTS1070-folded capillary cell in the automatic mode.

DNA Content Distribution in DNA Nanoparticles:

We analyzed the particles using the system previously described (Beh et al., 2014), which is herein incorporated by reference in its entirety. Plasmid DNA was labeled using Minis Bio Label IT® Tracker™ Intracellular Nucleic Acid Localization Kits, Cy5 (Minis Bio LLC. Madison, Wis.) and used to synthesize particles with /PEI with both bulk and FNC methods. These particles were individually measured for their fluorescent intensity at 670 nm using Cylindrical Illumination Correlation Spectroscopy and compared with free labeled DNA. The peak intensity was deconvolved using the naked labeled DNA as a control in order to obtain the distribution of particles with differing DNA content.

In Vitro Transfection of IPEI-g-PEG/DNA Complex Nanoparticles:

HeLa cells were maintained in Dulbecco's Modified Eagle's Medium (DMEM) supplemented with 10% FBS and 100 U/mL Penicillin/100 µg/mL Streptomycin, and cells were cultured at 37° C. and 5% $CO_2$. At 24 h prior to the transfection experiments, cells were seeded in 48-well plates at a density of $2 \times 10^4$ cells/well. Various nanoparticle solutions equivalent to 0.5 µg of DNA dose were added to the cells and incubated for 4 h, after which the media were refreshed. After 48 h, media were removed, and cells were washed with 1×PBS (pH 7.4). One hundred µL of reporter lysis buffer (Promega, Madison, Wis.) was added to each well. Cells were then subjected to two freeze-thaw cycles. Twenty µL of cell lysate from each well was assayed using a luciferase assay kit (Promega, Madison, Wis.) on a luminometer (20/20n, Turner BioSystems, Sunnyvale, Calif.). The luciferase activity was converted to the amount of luciferase expressed using a recombinant luciferase protein (Promega) as the standard and normalized against the total protein content in the lysate using a BCA assay (Pierce, Rockford, Ill.).

Results

The formulation of highly uniform /PEI/DNA complex nanoparticles in a large scale with a high degree of reproducibility is a key step for successful translation of these nanoparticles from bench to clinical application. In the present work, we demonstrated for the first time the use of the FNC process to generate PEC nanoparticles comprised of a cationic polymer, /PEI, and an anionic biopolymer, DNA. This process utilized confined precipitation geometries with two or more impinging fluid streams to achieve rapid mixing conditions yielding nanoparticles with well-defined size and narrow distribution (Johnson et al., Aiche J, 2003; D'Addio et al., 2011), which are herein incorporated by reference in their entireties. In the present study, we use a confined impinging jet (CIJ) device that allows both the high-throughput screening synthesis of nanoparticles in a smaller scale and larger scale production through continuous flow. FIG. 1A schematically shows the process employed herein and FIG. 1B, FIG. 1C, FIG. 1D, and FIG. 1E show representative embodiments of the device. Solutions of /PEI and DNA separately loaded in syringes are impinged at variable flow rates into a confined chamber using digitally programmable pumps. Process variables such as flow rate can affect the physiochemical properties (size, shape, and PDI) of the fabricated nanoparticles. To evaluate the role of the flow rate on the preparation of /PEI/DNA complex nanoparticles, experiments were run at different flow rates (1 mL/min, Reynold's number Re=95 up to 75 mL, Re=7,200) keeping the concentrations of DNA and PEI constant. Transmission electron microscopy (TEM) images (FIG. 2A, FIG. 2B, FIG. 2C, FIG. 2D, FIG. 2E, FIG. 2F, FIG. 3A, FIG. 3B, FIG. 3C, FIG. 3D, FIG. 3E, and FIG. 3F) of /PEI/DNA nanoparticles suggest a noticeable effect of the flow rate on particle size and distribution. For flow rates below 20 mL/min (Re<1,900, FIG. 2A and FIG. 2B) nanoparticles are bigger and more heterogeneous. On the other hand, smaller and homogeneous /PEI/DNA nanoparticles (average 30-40 nm) were generated for flow rates >20 mL/min (Re >1,900). The characteristic mixing time is a function of the flow rate. At low flow rates, the mixing time ($\tau_{mix}$) is not short enough to provide a homogeneous micromixing environment and hence the formation of larger and more heterogenous populations of nanoparticles. When the flow rates are high enough, the flow pattern assumes turbulent-like characteristics and the mixing time is on the order of a few milliseconds (<10 ms). Under these conditions, an efficient mass transfer was achieved, and discrete and narrow sized /PEI/DNA nanoparticles were produced. DLS analysis of /PEI/DNA nanoparticles prepared at various flow rates also indicates that the average size of nanoparticles is dependent on the flow rate reaching a plateau at flow rates above 20 mL/min (FIG. 4A), suggesting the limit of rapid mixing was achieved. These results are consistent with previous results observed for amphiphilic polymer nanoparticles prepared by the FNP method, where nanoparticle size becomes independent of flow rate for Re numbers above 1600 (Shen et al., 2011; Santos et al., 2014; Johnson et al., Phys. Rev. Lett., 2003; Johnson et al., Aiche J., 2003), which are herein incorporated by reference in their entireties. The final average particle size is a function of the mixing time, the concentration and chemical composition of components, and the specific time of nucleation and aggregation of each component (Santos et al., 2014; Johnson et al., Phys. Rev. Lett., 2003; Johnson et al., Aiche J., 2003), which are herein incorporated by reference in their entireties. To further illustrate the robustness and reproducibility of the /PEI/DNA nanoparticle formation process in a CIJ device, several batches of nanoparticles were prepared by different operators at different times. DLS data (FIG. 4B) shows no significant batch-to-batch variability. In addition, since the CIJ can operate in a continuous mode, the physiochemical properties of the nanoparticles are independent of batch size, and ensures the production of enough nanomaterials for clinical studies (>0.1 kg per day) and industrial scale production (>1 kg per day) (Kamaly et al., 2012), which is herein incorporated by reference in its entirety.

Having established the conditions at which one can produce /PEI/DNA nanoparticles with high reproducibility in a CIJ device, we investigated how DNA concentration might impact particle size and size distribution for both the FNC process and hulk precipitation counterpart. /PEI/DNA nanoparticles were prepared at DNA concentrations of 25, 50, and 100 µg/mL while keeping the /PEI concentration constant. Representative TEM images of the particles shown in FIG. 6A, FIG. 6B, FIG. 6C, FIG. 6D, FIG. 6E, and FIG. 6F indicate that /PEI/DNA nanoparticles prepared by FNC in a CIJ device at a flow rate of 20 mL/min (FIG. 6A, FIG. 6B, and FIG. 6C) are smaller and present excellent size distribution compared to the bulk mixing counterpart (FIG. 6D, FIG. 6E, and FIG. 6F) regardless of the initial amount of DNA used. The formation of smaller and uniform complex nanoparticles by FNC occurs because the mixing regime in the CU device is more precisely controlled than in bulk mixing. In addition, the intense mixing provided by the FNC process results in a mixing time that is much shorter (on the order of a few milliseconds) than the characteristic time of aggregation. On the contrary, the mixing nature in bulk mixing is very poorly defined resulting in more heterogenous particle size distribution. Interestingly, when the concentration of DNA was increased from 25 to 100 µg/mL in the FNC preparation (FIG. 6A, FIG. 6B, and FIG. 6C), nanoparticles underwent a morphological transition from pure spheres to short rod-like nanoparticles. In addition to providing a better control over particle size and distribution, FNC may be useful in the preparation of particles of different shape via fine-tuning of the conditions used in the process. Since FNC operates in a continuous mode, nanoparticles of different shape can be produced reproducibly, independent of the hatch size.

Figure 7D:
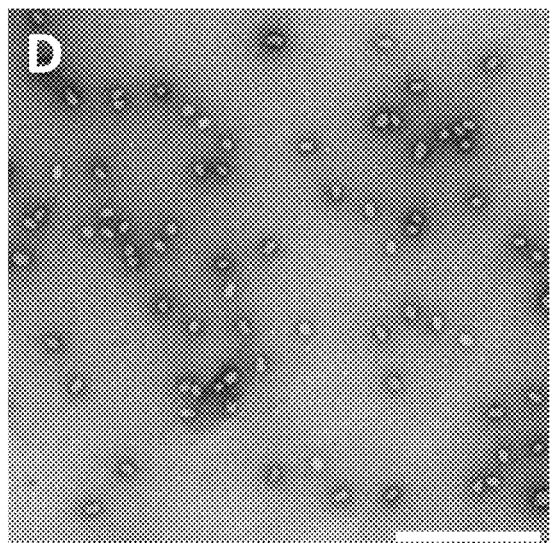

Formulation parameters and CU process variables play a role in determining the physiochemical properties of the fabricated nanoparticles, including particle size and uniformity. We sought to investigate the possibility of preparing /PEI/DNA nanoparticles of different shapes by FNC in a CIJ device through tuning for example the pH value of /PEI solutions. Together with size, nanoparticle shape is known to be one of the most influential variables in the physiological fate of nanoparticles. To prepare particles of different shapes in a CIJ device, the initial pH value of /PEI solution was adjusted before being impinged with DNA in the CIJ. As the pH value of the /PEI solution increased from 2.5 to 4.5, /PEI/DNA complex nanoparticles experience a significant shape transition, from very uniform and small spherical particles (30-40 nm) at pH 2.5 to a rod-like morphology at pH 4.5 (FIG. 7B, FIG. 7C, and FIG. 7D). Further increasing the pH of /PEI solution to 5.5 (FIG. 7A) significantly reduces the amount of spherical like particles present in solution (from 25%) at pH 4.5 to 12% at pH 5.5). This is consistent with the effect of /PEI net charge and its ability to effectively condense DNA. At low pH values (pH<3.5) /PEI is fully protonated and can more effectively condense DNA into spherical nanoparticles, whereas at high pH values (pH >4) the positive net charge of /PEI is significantly lower, rendering the polymer chain backbone stiffer which possibly translates into a distinct nanoparticle formation pathway.

A series of nanoparticles prepared via both the FNC and bulk mixing were evaluated for their DNA content within a nanoparticle distribution. Together with size and shape, the amount of DNA/nanoparticles plays a significant role in gene transfection. To analyze the composition distribution of DNA nanoparticles prepared by FNC, we used a single particle analysis method recently developed in our lab, (Beh et al., 2014), which is herein incorporated by reference in its entirety. The method employed herein, cylindrical illumination confocal spectroscopy (CICS), offers high detection uniformity and mass detection efficiency. /PEI-DNA complex nanoparticles were prepared using Cy5 labeled plasmid DNA and then passed through a microfluid chip to allow single particle measurement for their fluorescent intensity at 670 nm using CICS. The peak intensity was deconvoluted using free DNA as a control in order to obtain the distribution of particles with differing DNA content. 1PEI-DNA complex nanoparticles were prepared at a flow rate of 20 mL/min using 25 µg/mL DNA and a pH value of 3.5 for /PEI solution. Under these conditions highly uniform spheres are obtained by the FNC method. CICS analysis shows that the average number of DNA molecules per nanoparticle is slightly lower for complex particles prepared by FNC, 4.2 vs 4.8 DNA molecules for bulk mixing (FIG. 9A). While the average number of DNA molecules per particle was similar, the distribution of DNA/particle shows a notable difference. For /PEI-DNA complex nanoparticles prepared by FNC, the majority of particles contained 4 DNA molecules, whereas the ones prepared by bulk mixing mostly contained an average of 5 DNA molecules. This result is consistent with the observed nanoparticle average size determined by DLS and uniformity by TEM. Complex particles prepared by FNC are smaller and more uniform than particles prepared by bulk mixing.

Next, we measured the surface charge /PEI-DNA complex nanoparticles prepared by FNC using /PEI solutions at various pH values. Nanoparticles prepared by FNC have an average positive surface charge of +30 mV in water (FIG. 12B), regardless of the pH of /PEI solution. Similar values were observed for complex particles prepared by bulk mixing reflecting the high positive charge density of /PEI polymer. After incubation in physiological media, however, the surface charge of all particles dropped to +20 mV as a result of deprotonation of /PEI polymer and charge screening effect of complex nanoparticles in buffered solutions.

Shear is known to cause serious fragmentation of plasmid DNA into smaller molecular weight pieces. Shear rate in FNP processes can achieve values of ~9300 $s^{-1}$ for Re numbers 8000 (Luo et al., 2014), which is herein incorporated by reference in its entirety and which might be detrimental for biomacromolecules, such as DNA and large proteins. To assess possible fragmentation of DNA during particle formation in a CIJ device, naked DNA was impinged at flow rates varying from 1 mL/min up to 50 mL/min in the absence of /PEI. Samples were further analyzed by gel electrophoresis, and complexed with standard transfection reagents (jetPEI and Lipofectamine 2000) to be tested for transfection efficacy. As shown in FIG. 10 and FIG. 11, all DNA samples exposed to different flow rates presented similar bands and intensities compared to control DNA sample (absence of flow), suggesting DNA structure is not compromised by flow rate. To test if naked DNA exposed to high flow rates still maintained its bioactivity, we complexed DNA with standard transfection reagents including in vivo-jetPEI and Lipofectamine 2000 and its transfection efficiency was tested in vitro using a luciferase reporter plasmid DNA in HeLa cells. All DNA samples exposed to flow showed comparable levels of transfection efficiency (FIG. 12A, FIG. 12B, and FIG. 13) to those that were not exposed to flow, suggesting DNA was intact and fully bioactive.

/PEI/DNA complex nanoparticles prepared by FNC were evaluated for their transfection efficiency in HeLa cells. Transfection experiments were performed in the presence of 10% FBS and serum free media in a DNA dose dependent manner. As shown in FIG. 14A and FIG. 14B, the transfection efficiency increased as DNA dose increased from 0.1 μg/well to 0.5 μg/well. In addition, the transfection efficiency of particles in serum free media is significantly higher than in serum containing media, especially at lower DNA doses (0.1 or 0.2 μg DNA/well). The transfection levels achieved by /PEI-DNA complex nanoparticles prepared by FNC, however, were not significantly higher than the ones achieved by complex nanoparticles prepared via bulk mixing. Given /PEI is a highly effective transfection agent, we believe that the significant improvements in particle size and uniformlity provided by FNC are masked by the effectiveness of this transfection agent.

We also assessed the transfection efficacy of nanoparticles of different shape prepared by FNC. Nanoparticles prepared by the FNC method exhibited equivalent levels of transfection efficiency as those prepared by the batch mode mixing method at 200-μL scale. No significant differences in physicochemical properties and transfection efficiency were observed between the nanoparticles synthesized by the two methods.

Summary

We have successfully developed an efficient FNC process for continuous production of /PEI/DNA nanoparticles with uniform and small size. The method involves the complex coacervation of negatively charged DNA plasmid and positive charged/PEI under highly dynamic and homogeneous mixing conditions. The quality of the/PEI/DNA nanoparticles prepared with this process is dependent on several experimental parameters including flow rates of the solutions, pH of /PEI solution, N/P ratio, and concentrations of /PEI and DNA solutions. There is no significant batch-to-batch variability for the DNA nanoparticles prepared with this FNC method. More importantly, DNA sample remains intact and fully bioactive after being subjected to the flow conditions. The FNC prepared nanoparticles yielded the same transfection efficiency as those prepared with small scale batch-mode mixing. This FNC process can be applied for preparing DNA and RNA containing nanoparticles with other polycationic carriers. These results confirm that FNC is suitable for preparing polyelectrolyte coacervate (PEC) nanoparticles in clinical applications and industrial scale production.

Example 2

Chitosan/TPP Polyelectrolyte Complex Nanoparticles

Materials and Methods

Preparation of controllable size chitosan: TPP nanoparticle formulations: Discrete polyelectrolyte nanoparticles were prepared under rapid micromixing conditions using a confined impinging jet device with three high-velocity jets designed and built in our lab. In a typical procedure, oppositely charged biomacromolecule solutions are loaded into separated syringes and fed into a confined chamber by digitally controlled syringe pumps (New Era Pump System, model NE-4000). A long tube runner serving as outlet (represented by the arrow) is used to ensure that all biomacromolecules brought into confined chamber by the opposing streams are fully reacted before collection. A third jet was added, to for instance control the polarity, salt concentration or to allow the addition of a cryoprotectant in situ during nanoparticle formation, without affecting the performance of the device.

Discrete chitosan:TPP nanoparticles of various sizes were prepared either by tuning the flow rate or through optimization of formulation conditions (e.g. pH value of chitosan solution, chitosan and TPP concentration). Chitosan was dissolved in acetic acid 0.5% v/v at a final concentration of 0.5 mg/mL for 24 h. The final pH was adjusted to 3.5, 5.0 and 6.5, respectively, just prior to formulation. TPP was dissolved in water at a 0.25 mg/mL. The solutions were loaded into separated syringes, and the nanoparticles were prepared in the CIJ-3i device as described above.

Results

As shown in FIG. 15, flow rate significantly influenced average particle size and its polydispersity. At high flow rates (>10 mL/min) the average particle size as well as its polydispersity becomes flow independent. Under these conditions, discrete and highly uniform (PDI 0.05) nanoparticles of 60 nm (as given by the Z-average) were obtained. For lower flow rates (<10 mL/min), the significant increase in particle size (Dh=140 nm at a flow rate of 1 mL/min) is accompanied by a decrease in particle uniformity. FIG. 16A, FIG. 16B, and FIG. 16C show the preparation of chitosan: TPP nanoparticles of tunable sizes and surface charge through optimization of formulation conditions. Chitosan solutions of pH values 3.5, 5.0 and 6.5 were used. At pH 3.5, formulated nanoparticles have a size of 20 nm and a surface charge of 28 mV (FIG. 16A, FIG. 16B, and FIG. 16C). On the other hand, particles of 60 nm on average and surface charge of 9 mV are obtained when a chitosan solution of pH 6.5 is used. Chitosan nanoparticles of intermediate size (40 nm) and charge (19 mV) result when a chitosan solution of pH 5 is used. TEM images (FIG. 17A, FIG. 17B, and FIG. 17C) corroborate that all conditions used resulted in the formulation of highly uniform and discrete spherical nanoparticles with well-defined size.

Stability of Chitosan:

TPP nanoparticles in relevant biological medium (salt and serum stability): For drug delivery applications, nanoparticles should be stable in physiological concentrations of salt and protein solutions. Aggregation of nanoparticles under these conditions significantly impacts their physiochemical properties often resulting in rapid clearance by macrophages and poor biodistribution. Rapid micromixing provides improved mixing conditions when compared to bulk mixing, and the resultant nanoparticles are expected to be highly condensed and compact through better polymer chain entanglement. To evaluate salt and serum stability, we prepared chitosan:TPP nanoparticles using chitosan solution at pH 5 as described above but with a slight modification. For salt stability studies, the third jet was loaded with PBS 3× concentrated and nanoparticles were prepared at a flow rate of 20 mL/min resulting in a formulation with a final concentration of PBS equal to 1× and a final pH of 6.7. Particles were left in this medium for 5 days.

Chitosan: TPP nanoparticles remains unaltered over the period of time analyzed: DLS data (FIG. 18A, FIG. 18B, FIG. 18C, FIG. 18D, and FIG. 18E) shows that both particle size (inset in FIG. 18A) and size distribution remains unaltered over the period of time analyzed. TEM images of chitosan:TPP nanoparticles taken at day 3 (FIG. 18D) and 5 (FIG. 18E) further confirms that chitosan:TPP nanoparticles were successfully prepared in high salt concentration and remained stable during at least 5 days. In addition, we assessed nanoparticle stability in FBS 2% v/v over a 3 h period. Nanoparticles formed by fast mixing shows good stability with no signs of aggregation (FIG. 18B).

CIJ-3i as a versatile platform for the preparation of several polyelectrolyte nanoparticles: To show the versatility of the CIJ-3i in regards to the choice of charged polymers, we prepared polyelectrolyte nanoparticles of different chemical properties, size and shape, using several oppositely charged biomacromolecules. For instance, we were able to prepare discrete and highly uniform chitosan:Glu5 (a pentablock glutamic acid peptide) nanoparticles of 100 nm (FIG. 19A). 50 nm nanoparticles were prepared when using chitosan-g-PEG 17 (0.5 mg/mL, pH 5.0, 2% PEG 17K grafting) and Glu5 (0.5 mg/mL, pH=9) (FIG. 19B). Short rod-like particles of 30-60 nm are obtained when chitosan (0.5 mg/mL, pH 3.5) and poly-aspartic acid sodium salt (0.25 mg/mL, pH=9.2) are complexed at 25 mL/min (FIG. 19D). In another instance, 10-15 nm nanoparticles were obtained after fast complexation of protamine sulfate (0.25 mg/mL) and heparin (1 mg/mL) solution (FIG. 19C).

Encapsulation of biological therapeutics: Efficient encapsulation of water-soluble therapeutics such as proteins, cytokines and nucleic acids is paramount in the pharmaceutical industry. We used BSA as a model protein in our encapsulation and release studies. To determine the encapsulation efficiency of BSA, BSA (0.25 mg/mL) was dissolved in a solution of TPP (0.25 mg/mL) and homogenized for 30 min at room temperature (RT) before use. Low molecular weight chitosan (LMWC) solution was prepared at 0.5 mg/mL in acetic acid (0.5% v/v) for 24 h at RT, and its pH adjusted to 5 before use. Both solutions were independently loaded into 10 mL syringes and then BSA-containing chitosan NPs were prepared in the CIJ-3i using a flow rate of 20 mL/min. The nanoparticles were purified by ultracentrifugation (700 g to avoid particle sedimentation) using a membrane with a molecular weight cutoff (MWCO) of 100 kDa. The purification step was repeated till no free BSA was detected in the lysate (4× in average). The encapsulation efficiency was determined using BCA assay and the following equation:

$$EE(\%) = \frac{\text{amount of protein in } Chitosan\ NPS}{\text{Total amount Amount of Protein}} \times 100 \quad (3)$$

As shown in Table 1, we were able to achieve 90% encapsulation of BSA in chitosan:TPP nanoparticles in a CIJ-3i device. The amount of BSA encapsulated was dependent on the pH of the chitosan solution, being smaller (EE 70%) when the pH of the chitosan solution as about 3.5. In addition, BSA-containing chitosan nanoparticles have a comparable number average size and surface charge, and identical particle size distribution to empty chitosan nanoparticles (FIG. 20A, FIG. 20B, and FIG. 20C). The fast and homogeneous mixing conditions achieved in the CIJ-3i proves successful in retaining particle size and morphology (FIG. 20E) in spite of the high content of protein encapsulated.

TABLE 1

Encapsulation efficiency of BSA protein in chitosan nanoparticles using a CIJ-3i.

| pH of Chitosan Solution | EE % |
| --- | --- |
| 3.5 | 69.2 + 1.9 |
| 5.0 | 90.4 + 1.4 |

For the release studies, rhodamine-labeled BSA (rhod-BSA) at a concentration of 0.1 mg/mL is used. Release studies were performed in PBS 10 mM solution, pH 5.5 and 7.2, at 37° C. Samples (1 mL) were taken at predefined time points and the volume replaced with fresh PBS of appropriate pH. Nanoparticles are centrifuged at 15 000 g for 30 min at 4° C., the supernatant collected, and the mount of protein released is measured by fluorescence. As shown in FIG. 21, an initial burst release of BSA is observed within the first 6 hours, followed by a more gradual release thereafter.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Baum, C.; O. Kustikova, U. Modlich, Z. Li, B. Fehse, Hum Gene Ther 2006, 17, 253.

Beh, C. W.; Pan, D.; Lee, J.; Jiang, X.; Liu, K. J.; Mao, H. Q.; Wang, T. H. Direct interrogation of DNA content distribution in nanoparticles by a novel microfluidics-based single-particle analysis. Nano Lett 2014, 14, 4729-35.

Bertrand, N.; J. Wu, X. Xu, N. Kamaly, O. C. Farokhzad, Advanced Drug Delivery Reviews 2014, 66, 2.

Bessis, N., GarciaCozar, F. J., Boissier, M. C., Gene Ther 2004, 11 Suppl 1, S10.

Bonnet, M.-E.; P. Erbacher, A.-L. Bolcato-Bellemin, Pharmaceutical Research 2008, 25, 2972.

Buscail, L.; B. Bournet, F. Vernejoul, G. Cambois, H. Lulka, N. Hanoun, M. Dufresne, A. Meulle, A. Vignolle-Vidoni, L. Ligat, N. Saint-Laurent, F. Pont, S. Dejean, M. Gayral, F. Martins, J. Torrisani, O. Barbey, F. Gross, R. Guimbaud, P. Otal, F. Lopez, G. Tiraby, P. Cordelier, Mol Ther 2015, 23, 779.

Chauhan, V. P., Jain, R. K., Nature Materials 2013, 12, 958.

D'Addio, S. M.; Prud'homme, R. K. Controlling drug nanoparticle formation by rapid precipitation. *Advanced Drug Delivery Reviews* 2011, 63, 417-426.

D'Addio, S. M.; Saad, W.; Ansell, S. M.; Squiers, J. I.; Adamson, D. H.; Herrera-Alonso, M.; Wohl, A. R.; Hoye, T. R.; Macosko, C. W.; Mayer, L. D.; Vauthier, C.; Prud'homme, R. K. Effects of block copolymer properties on nanocarrier protection from in vivo clearance. *Journal of controlled release: official journal of the Controlled Release Society* 2012, 162, 208-217.

D'Addio, S. M.; Baldassano, S.; Shi, L.; Cheung, L. L.; Adamson, D. H.; Bruzek, M.; Anthony, J. E.; Laskin, D. L.; Sinko, P. J.; Prud'homme, R. K. Optimization of cell receptor-specific targeting through multivalent surface decoration of polymeric nanocarriers. *Journal of controlled release: official journal of the Controlled Release Society* 2013, 168, 41-49.

Gindy, M. E.; Ji, S. X.; Hoye, T. R.; Panagiotopoulos, A. Z.; Prud'homme, R. K. Preparation of Poly(ethylene glycol) Protected Nanoparticles with Variable Bioconjugate Ligand Density. *Biomacromolecules* 2008, 9, 2705-2711.

Ginn, S. L.; I. E. Alexander, M. L. Edelstein, M. R. Abedi, J. Wixon, J Gene Med 2013, 15, 65.

Han, J.; Zhu, Z. X.; Qian, H. T.; Wohl, A. R.; Beaman, C. I.; Hoye, T. R.; Macosko, C. W. A simple confined impingement jets mixer for flash nanoprecipitation. *J Pharm Sci-Us* 2012, 101, 4018-4023.

Ho, Y. P.; Grigsby, C. L.; Zhao, F.; Leong, K. W. Tuning Physical Properties of Nanocomplexes through Microfluidics-Assisted Confinement. *Nano Lett* 2011, 11, 2178-2182.

Jere, D.; H. L. Jiang, R. Arote, Y. K. Kim, Y. J. Choi, M. H. Cho, T. Akaike, C. S. Cho, Expert Opinion on Drug Delivery 2009, 6, 827.

Johnson, B. K.; Prud'homme, R. K. Chemical processing and micromixing in confined impinging jets. *Aiche J* 2003, 49, 2264-2282.

Johnson, B. K.; Prud'homme, R. K. Flash NanoPrecipitation of organic actives and block copolymers using a confined impinging jets mixer. *Aust J Chem* 2003, 56, 1021-1024.

Johnson, B. K.; Prud'homme, R. K. Mechanism for rapid self-assembly of block copolymer nanoparticles. *Physical review letters* 2003, 91, 118302.

Kamaly, N.; Xiao, Z.; Valencia, P. M.; Radovic-Moreno, A. F.; Farokhzad, 0. C. Targeted polymeric therapeutic nanoparticles: design, development and clinical translation. *Chemical Society reviews* 2012, 41, 2971-3010.

Kolishetti, N.; Dhar, S.; Valencia, P. M.; Lin, L. Q.; Kamik, R.; Lippard, S. J.; Langer, R.; Farokhzad, O. C. Engineering of self-assembled nanoparticle platform for precisely controlled combination drug therapy. *Proceedings of the National Academy of Sciences of the United States of America* 2010, 107, 17939-44.

Lewis, D. R.; Petersen, L. K.; York, A. W.; Zablocki, K. R.; Joseph, L. B.; Kholodovych, V.; Prud'homme, R. K.; Uhrich, K. E.; Moghe, P. V. Sugar-based amphiphilic nanoparticles arrest atherosclerosis in vivo. *P Natl Acad Sci USA* 2015, 112, 2693-2698.

Lim, J. M., A. Swami, L. M. Gilson, S. Chopra, S. Choi, J. Wu, R. Langer, R. Karnik, O. C. Farokhzad, Acs Nano 2014, 8, 6056.

Luo, H. Y.; Santos, J. L.; Herrera-Alonso, M. Toroidal structures from brush amphiphiles. *Chem Commun* 2014, 50, 536-538.

Mangraviti, A.; Tzeng, S. Y.; Kozielski, K. L.; Wang, Y.; Jin, Y.; Gullotti, D.; Pedone, M.; Buaron, N.; Liu, A.; Wilson, D. R.; Hansen, S. K.; Rodriguez, F. I.; Gao, G. D.; DiMeco, F.; Brem, H.; Olivi, A.; Tyler, B.; Green, J. J. Polymeric nanoparticles for nonviral gene therapy extend brain tumor survival in vivo. *ACS Nano* 2015, 9, 1236-49.

Mastorakos, P.; da Silva, A. L.; Chisholm, J.; Song, E.; Choi, W. K.; Boyle, M. P.; Morales, M. M.; Hanes, J.; Suk, J. S. Highly compacted biodegradable DNA nanoparticles capable of overcoming the mucus barrier for inhaled lung gene therapy. *Proceedings of the National Academy of Sciences of the United States of America* 2015.

Mura, S., J. Nicolas, P. Couvreur, Nature Materials 2013, 12, 991.

Murday, J. S.; Siegel, R. W.; Stein, J.; Wright, J. F. Translational nanomedicine: status assessment and opportunities. *Nanomedicine: nanotechnology, biology, and medicine* 2009, 5, 251-73.

Pack, D. W., Hoffman, A. S., Pun, S., Stayton, P. S., Nature Reviews Drug Discovery 2005, 4, 581.

Patnaik, S., K. C. Gupta, Expert Opinion on Drug Delivery 2013, 10, 215.

Peer, D.; J. M. Karp, S. Hong, O. C. FaroKhzad, R. Margalit, R. Langer, Nature Nanotechnology 2007, 2, 751.

Romanowsky, M. B.; Abate, A. R.; Rotem, A.; Holtze, C.; Weitz, D. A. High throughput production of single core double emulsions in a parallelized microfluidic device. *Lab on a chip* 2012, 12, 802-7.

Santos, J. L.; Herrera-Alonso, M. Kinetically Arrested Assemblies of Architecturally Distinct Block Copolymers. *Macromolecules* 2014, 47, 137-145.

Shen, H.; Hong, S. Y.; Prud'homme, R. K.; Liu, Y. Self-assembling process of flash nanoprecipitation in a multi-inlet vortex mixer to produce drug-loaded polymeric nanoparticles. *J Nanopart Res* 2011, 13, 4109-4120.

Valencia, P. M.; Farokhzad, O. C.; Karnik, R.; Langer, R. Microfluidic technologies for accelerating the clinical translation of nanoparticles. *Nat Nanotechnol* 2012, 7, 623-9.

Wightman, L., Kircheis, R., Rossler, V., Carotta, S., Ruzicka, R., Kursa, M., Wagner, E., Journal of Gene Medicine 2001, 3, 362.

Yang, J.; Hendricks, W.; Liu, G. S.; McCaffery, J. M.; Kinzler, K. W.; Huso, D. L.; Vogelstein, B.; Zhou, S. B. A nanoparticle formulation that selectively transfects metastatic tumors in mice. *P Natl Acad Sci USA* 2013, 110, 14717-14722.

Yin, H.; R. L. Kanasty, A. A. Eltoukhy, A. J. Vegas, J. R. Dorkin, D. G. Anderson, Nat Rev Genet 2014, 15, 541.

Zhu, Z. X. Flash Nanoprecipitation: Prediction and Enhancement of Particle Stability via Drug Structure. *Molecular pharmaceutics* 2014, 11, 776-786.

Although the foregoing subject matter has been described in some detail by way of illustration and example for purposes of clarity of understanding, it will be understood by those skilled in the art that certain changes and modifications can be practiced within the scope of the appended claims That which is claimed:

1. A nanoparticle or a plurality of nanoparticles comprising a polyelectrolyte complex (PEC) prepared by a flash nanocomplexation (FNC) method, wherein the nanoparticle or plurality of nanoparticles comprises one or more water-soluble polycationic polymers and one or more water-soluble polyanionic polymers and has a uniform size and shape and a low polydispersity index (PDI), wherein the plurality of PEC nanoparticles has a polydispersity index (PDI) selected from the group consisting of: between about 0.05 to about 0.2; between about 0.05 to 0.1; and about 0.05 and an average size between about 20 nm to about 500 nm.

2. The nanoparticle or plurality of nanoparticles of claim 1, wherein the one or more water-soluble polycationic polymers is selected from the group consisting of polyethylenimine, chitosan, a PAMAM dendrimer, protamine, poly(arginine), poly(lysine), a poly(beta-aminoester), a cationic peptide, a positively charged block copolymer, and derivatives thereof.

3. The nanoparticle or plurality of nanoparticles of claim 1, wherein the polyethylenimine comprises linear polyethylenimine.

4. The nanoparticle or plurality of nanoparticles of claim 1, wherein the one or more water-soluble polyanionic polymers is selected from the group consisting of poly(aspartic acid), poly(glutamic acid), a negatively charged block copolymer, heparin sulfate, dextran sulfate, hyaluronic acid, alginate, tripolyphosphate (TPP), oligo(glutamic acid), a cytokine, a protein, a peptide, a growth factor, and a nucleic acid.

5. The nanoparticle or plurality of nanoparticles of claim 4, wherein the nucleic acid is selected from the group consisting of an antisense oligonucleotide, cDNA, genomic DNA, guide RNA, plasmid DNA, vector DNA, mRNA, miRNA, piRNA, shRNA, and siRNA.

6. The nanoparticle or plurality of nanoparticles of claim 5, wherein the nucleic acid comprises a plasmid DNA.

7. The nanoparticle or plurality of nanoparticles of claim 1, wherein the one or more water-soluble polycationic polymers comprises polyethylenimine and the one or more water-soluble polyanionic polymers comprises plasmid DNA.

8. The nanoparticle or plurality of nanoparticles of claim 7, wherein the nanoparticle has a ratio of amine in the polyethylenimine to phosphate in the plasmid DNA of about 8.

9. The nanoparticle or plurality of nanoparticles of claim 1, wherein the nanoparticle has an average particle size selected from the group consisting of: between about 25 nm to about 100 nm; between about 30 nm to about 80; between about 25 nm to about 60 nm; between about 30 nm to about 45 nm; and about 30 nm.

10. The nanoparticle or plurality of nanoparticles of claim 1, wherein the nanoparticle has a shape selected from the group consisting of a sphere, a rod, and combinations thereof.

11. The nanoparticle or plurality of nanoparticles of claim 1, wherein the nanoparticle has an average number of water-soluble polyanionic polymers per nanoparticle of about 4.2.

12. The nanoparticle or plurality of nanoparticles of claim 1, wherein the nanoparticle has an average positive surface charge of about +30 mV in water or about +20 mV in a buffered solution.

13. The nanoparticle or plurality of nanoparticles of claim 1, wherein the water-soluble polycationic polymer is chitosan.

14. The nanoparticle or plurality of nanoparticles of claim 13, further comprising tripolyphosphate (TPP) and a protein, wherein the protein is co-encapsulated by the TPP and chitosan.

15. The nanoparticle or plurality of nanoparticles of claim 1, further comprising one or more water-soluble therapeutic agents selected from the group consisting of a small molecule, carbohydrate, sugar, protein, peptide, nucleic acid, antibody or antibody fragment thereof, hormone, hormone receptor, receptor ligand, cytokine, and growth factor.

16. The nanoparticle or plurality of nanoparticles of claim 1, further comprising one or more cryoprotectants.

17. The nanoparticle or plurality of nanoparticles of claim 1, wherein the one or more water-soluble polycationic polymers is polyethylenimine and the nucleic acid is plasmid DNA.

18. The nanoparticle or plurality of nanoparticles of claim 17, wherein the plurality of PEC nanoparticles has an average size between about 30 nm and about 40 nm.

* * * * *